(12) United States Patent
An et al.

(10) Patent No.: US 11,497,433 B2
(45) Date of Patent: Nov. 15, 2022

(54) BALANCE COMPENSATING DEVICE, BODY CENTER MEASURING APPARATUS, BALANCE COMPENSATION SYSTEM, AND BALANCE COMPENSATION METHOD

(71) Applicant: Anchor Logics Co., Ltd., Seoul (KR)

(72) Inventors: Ki Chul An, La Verne, CA (US); Yeonu An, La Verne, CA (US)

(73) Assignee: Anchor Logics Co., Ltd., Seoul (KR)

(*) Notice: Subject to any disclaimer, the term of this patent is extended or adjusted under 35 U.S.C. 154(b) by 0 days.

(21) Appl. No.: 17/168,314

(22) Filed: Feb. 5, 2021

(65) Prior Publication Data

US 2021/0161458 A1 Jun. 3, 2021

Related U.S. Application Data

(63) Continuation of application No. 16/443,339, filed on Jun. 17, 2019, now abandoned, which is a
(Continued)

(30) Foreign Application Priority Data

Apr. 10, 2018 (KR) .................. 10-2018-0041774
Dec. 6, 2018 (KR) .................. 10-2018-0156318
Mar. 27, 2019 (KR) .................. 10-2019-0034851

(51) Int. Cl.
*A61B 5/00* (2006.01)
*A61B 5/11* (2006.01)
(Continued)

(52) U.S. Cl.
CPC .......... *A61B 5/4023* (2013.01); *A61B 5/1101* (2013.01); *A63B 26/003* (2013.01);
(Continued)

(58) Field of Classification Search
CPC ... A61B 5/1036; A61B 5/4023; A61B 5/1101; A61B 5/1071; A63B 21/065;
(Continued)

(56) References Cited

U.S. PATENT DOCUMENTS 5,919,149 A 7/1999 Allum
6,063,046 A 5/2000 Allum
(Continued)

FOREIGN PATENT DOCUMENTS

JP 2004-130142 A 4/2004
JP 2016-209546 A 12/2016
(Continued)

OTHER PUBLICATIONS

An International Search Report and Written Opinion issued by the International Searching Authority dated Aug. 2, 2019 in connection with International application No. PCT/US2019/026843.
(Continued)

*Primary Examiner* — Patrick Fernandes
(74) *Attorney, Agent, or Firm* — Trop, Pruner & Hu, P.C.

(57) ABSTRACT

An apparatus for determining balance compensation includes a platform, sensors and a processor. The platform is configured for a person to stand on the platform. The sensors are coupled to the platform and measure at least one of a weight and a pressure. The processor determines a balance of the person based on the measurements of the sensors.

16 Claims, 31 Drawing Sheets

Related U.S. Application Data continuation of application No. 16/380,881, filed on Apr. 10, 2019, now abandoned.

(51) Int. Cl.
  *A63B 26/00* (2006.01)
  *A63B 21/065* (2006.01)
  *A61B 5/107* (2006.01)
  *A61F 5/02* (2006.01)

(52) U.S. Cl.
  CPC .............. *A61B 5/1071* (2013.01); *A61F 5/02* (2013.01); *A63B 21/065* (2013.01)

(58) Field of Classification Search
  CPC ......... A63B 26/003; G01G 19/44; A61F 5/02; A61N 1/36067
  See application file for complete search history.

(56) References Cited

U.S. PATENT DOCUMENTS

| | | | |
|---|---|---|---|
| 7,708,673 B2* | 5/2010 | Gibson-Horn | A61F 5/02 482/105 |
| 8,974,402 B2 | 3/2015 | Oddsson et al. | |
| 9,202,386 B2* | 12/2015 | Yuasa | A61B 5/1036 |
| 9,302,046 B1* | 4/2016 | Giuffrida | A61B 5/6826 |
| RE46,069 E | 7/2016 | GibsonHorn et al. | |
| 2004/0163855 A1 | 8/2004 | Carlucci | |
| 2006/0251334 A1 | 11/2006 | Oba et al. | |
| 2006/0293613 A1 | 12/2006 | Fatehi et al. | |
| 2010/0023293 A1 | 1/2010 | Walthert | |
| 2011/0043755 A1 | 2/2011 | Gibson-Horn et al. | |
| 2014/0330171 A1 | 11/2014 | Pan et al. | |
| 2016/0038060 A1 | 2/2016 | Kitamura et al. | |
| 2016/0051793 A1 | 2/2016 | Gibson-Horn | |
| 2016/0189371 A1 | 6/2016 | Krishna Rao et al. | |
| 2017/0135612 A1 | 5/2017 | Singhatat | |
| 2018/0336969 A1* | 11/2018 | Jabourian | G16H 50/30 |

FOREIGN PATENT DOCUMENTS

| | | |
|---|---|---|
| KR | 10-2008-0102466 A | 1/2008 |
| KR | 10-1052202 B1 | 7/2011 |
| KR | 10-1786846 B1 | 10/2017 |

OTHER PUBLICATIONS

"Portal Frames", SteelConstructions.info, downloaded on Jul. 6, 2021 from https://www.steelconstruction.info/Portal_frames.

European Patent Office, Office Action dated Nov. 16, 2021 in European Patent Application No. 19784761.9 (7 pages).

European Patent Office, Communication Under Rule 71(3) EPC dated Aug. 12, 2022 in European Patent Application No. 19784761.9 (90 pages).

* cited by examiner

FIG. 12

|  | LC1 | LC2 | LC3 | LC4 |  | CGx | CGy |
|---|---|---|---|---|---|---|---|
| 06:53.8 | 25.56 | 20.7 | 25.37 | 30.27 | 101.9 | -0.94 | 0.9 |
| 06:54.8 | 24.16 | 21.49 | 27.44 | 28.89 | 101.99 | -0.39 | 1.02 |
| 06:55.8 | 22.89 | 21.42 | 29.11 | 28.5 | 101.91 | -0.08 | 1.28 |
| 06:56.8 | 23.67 | 22.51 | 28.24 | 27.35 | 101.78 | -0.03 | 0.9 |
| 06:57.8 | 22.79 | 21.33 | 29.3 | 28.44 | 101.85 | -0.06 | 1.31 |
| 06:58.8 | 23.3 | 21.21 | 28.63 | 28.74 | 101.88 | -0.21 | 1.23 |
| 06:59.8 | 23.17 | 21.82 | 28.92 | 27.94 | 101.85 | -0.03 | 1.14 |
| 07:00.8 | 22.47 | 20.99 | 29.65 | 28.8 | 101.92 | -0.06 | 1.44 |
| 07:01.8 | 22.56 | 21.38 | 29.48 | 28.45 | 101.87 | -0.01 | 1.34 |
| 07:02.8 | 23.65 | 22.18 | 28.12 | 27.79 | 101.74 | -0.11 | 0.97 |
| 07:03.8 | 23.23 | 21.76 | 28.45 | 28.39 | 101.83 | -0.14 | 1.14 |
| 07:04.8 | 22.84 | 20.98 | 28.75 | 29.31 | 101.88 | -0.23 | 1.37 |
| 07:05.8 | 23.11 | 21.35 | 28.55 | 28.87 | 101.87 | -0.2 | 1.24 |
| 07:06.8 | 23.86 | 21.72 | 27.54 | 28.75 | 101.87 | -0.32 | 1.03 |
| 07:07.8 | 22.97 | 21.21 | 28.69 | 28.97 | 101.85 | -0.2 | 1.29 |
| 07:08.8 | 23.31 | 21.44 | 28.26 | 28.82 | 101.82 | -0.23 | 1.18 |
| 07:09.8 | 23.45 | 21.75 | 28.19 | 28.42 | 101.82 | -0.19 | 1.1 |
| 07:10.8 | 23.23 | 21.35 | 28.35 | 28.87 | 101.81 | -0.23 | 1.21 |
| 07:11.8 | 22.51 | 20.81 | 29.12 | 29.41 | 101.85 | -0.19 | 1.46 |
| 07:12.8 | 22.36 | 21 | 29.34 | 29.09 | 101.79 | -0.11 | 1.45 |
| 07:13.8 | 22.39 | 20.86 | 29.34 | 29.21 | 101.81 | -0.13 | 1.47 |
| 07:14.8 | 22.9 | 21.65 | 28.86 | 28.46 | 101.87 | -0.08 | 1.23 |
| 07:18.6 | 23.83 | 22.2 | 28.09 | 27.74 | 101.85 | -0.12 | 0.94 |
| 07:19.6 | 23.07 | 21.73 | 28.6 | 28.46 | 101.87 | -0.12 | 1.18 |
| 07:20.6 | 20.79 | 22.87 | 27.77 | 30.22 | 101.64 | -0.04 | 1.38 |
| 07:21.6 | 22.58 | 23.09 | 26.93 | 29.11 | 101.71 | -0.16 | 1 |
| 07:22.6 | 21.55 | 25.1 | 24.99 | 30.03 | 101.67 | -0.14 | 0.8 |
| 07:23.6 | 21.6 | 25.55 | 24.67 | 29.86 | 101.68 | -0.12 | 0.71 |
| 07:24.6 | 21.51 | 25.9 | 24.65 | 29.7 | 101.75 | -0.06 | 0.67 |
| 07:25.6 | 22.18 | 25.47 | 25.21 | 28.74 | 101.6 | -0.02 | 0.61 |
| 07:26.6 | 24.53 | 23.5 | 27.02 | 26.79 | 101.84 | -0.08 | 0.55 |
| 07:27.6 | 23.82 | 23 | 27.57 | 27.36 | 101.75 | -0.06 | 0.78 |
| 07:28.6 | 23.33 | 22.76 | 27.91 | 27.85 | 101.86 | -0.05 | 0.93 |
| 07:29.6 | 22.37 | 21.52 | 29.37 | 28.46 | 101.73 | 0.01 | 1.34 |
| 07:30.6 | 22.64 | 21.28 | 29.21 | 28.7 | 101.84 | -0.08 | 1.34 |
| 07:31.6 | 22.15 | 21.33 | 28.53 | 29.67 | 101.69 | -0.19 | 1.41 |

FIG. 13

| | W1 | Wx | Wy | W2 |
|---|---|---|---|---|
| 06:53.8 | 3.391586119 | -2.449769821 | 2.345524297 | 4.795294118 |
| 06:54.8 | 2.848459364 | -1.01729156 | 2.660608696 | 3.677900256 |
| 06:55.8 | 3.342693777 | -0.208511509 | 3.336184143 | 3.544695652 |
| 06:56.8 | 2.344063322 | -0.078092072 | 2.342762148 | 2.42085422 |
| 06:57.8 | 3.41594305 | -0.15629156 | 3.412365729 | 3.568657289 |
| 06:58.8 | 3.251295816 | -0.547181586 | 3.204920716 | 3.752102302 |
| 06:59.8 | 2.970567698 | -0.07814578 | 2.969539642 | 3.047685422 |
| 07:00.8 | 3.756832347 | -0.156398977 | 3.753575448 | 3.909974425 |
| 07:01.8 | 3.491294145 | -0.026053708 | 3.491196931 | 3.517250639 |
| 07:02.8 | 2.540162067 | -0.286225064 | 2.523984655 | 2.810209719 |
| 07:03.8 | 2.991260993 | -0.364608696 | 2.968956522 | 3.333565217 |
| 07:04.8 | 3.619664596 | -0.599294118 | 3.56970844 | 4.169002558 |
| 07:05.8 | 3.272412158 | -0.521074169 | 3.230659847 | 3.751734015 |
| 07:06.8 | 2.810058834 | -0.83371867 | 2.683531969 | 3.517250639 |
| 07:07.8 | 3.400414146 | -0.520971867 | 3.360268542 | 3.881240409 |
| 07:08.8 | 3.130655908 | -0.598941176 | 3.072828645 | 3.671769821 |
| 07:09.8 | 2.906918015 | -0.494777494 | 2.864501279 | 3.359278772 |
| 07:10.8 | 3.207055461 | -0.598882353 | 3.150641944 | 3.749524297 |
| 07:11.8 | 3.835163335 | -0.494923274 | 3.803094629 | 4.298017903 |
| 07:12.8 | 3.785667537 | -0.286365729 | 3.774820972 | 4.061186701 |
| 07:13.8 | 3.842577866 | -0.338498721 | 3.827639386 | 4.166138107 |
| 07:14.8 | 3.211377185 | -0.208429668 | 3.204606138 | 3.413035806 |
| 07:18.6 | 2.468439255 | -0.31258312 | 2.448567775 | 2.761150895 |
| 07:19.6 | 3.090193884 | -0.312644501 | 3.074337596 | 3.386982097 |
| 07:20.6 | 3.588800751 | -0.10397954 | 3.587294118 | 3.691273657 |
| 07:21.6 | 2.634364729 | -0.416204604 | 2.601278772 | 3.017483376 |
| 07:22.6 | 2.111817525 | -0.364035806 | 2.080204604 | 2.444240409 |
| 07:23.6 | 1.872548869 | -0.312061381 | 1.846363171 | 2.158424552 |
| 07:24.6 | 1.750519497 | -0.156138107 | 1.743542199 | 1.899680307 |
| 07:25.6 | 1.585915666 | -0.051969309 | 1.585063939 | 1.637033248 |
| 07:26.6 | 1.44760671 | -0.208368286 | 1.432531969 | 1.640900256 |
| 07:27.6 | 2.035791851 | -0.156138107 | 2.029795396 | 2.185933504 |
| 07:28.6 | 2.426256005 | -0.130255754 | 2.422757033 | 2.553012788 |
| 07:29.6 | 3.486496057 | 0.026017903 | 3.486398977 | 3.51241688 |
| 07:30.6 | 3.496383214 | -0.208368286 | 3.490168798 | 3.698537084 |
| 07:31.6 | 3.700225572 | -0.49414578 | 3.667081841 | 4.161227621 |
| AVERAGE | 2.973930092 | -0.390703396 | 2.917980747 | 3.310129582 |

FIG. 14

|  | x-axis fluctuation lb | | y-axis fluctuation lb | |
|---|---|---|---|---|
| 06:53.8 | 2.059066 | | 0.572456 | |
| 06:54.8 | 0.626588 | | 0.257372 | |
| 06:55.8 | | -0.18219 | | -0.4182 |
| 06:56.8 | | -0.31261 | 0.575219 | |
| 06:57.8 | | -0.23441 | | -0.49438 |
| 06:58.8 | 0.156478 | | | -0.28694 |
| 06:59.8 | | -0.31256 | | -0.05156 |
| 07:00.8 | | -0.2343 | | -0.83559 |
| 07:01.8 | | -0.36465 | | -0.57322 |
| 07:02.8 | | -0.10448 | 0.393996 | |
| 07:03.8 | | -0.02609 | | -0.05098 |
| 07:04.8 | 0.208591 | | | -0.65173 |
| 07:05.8 | 0.130371 | | | -0.31268 |
| 07:06.8 | 0.443015 | | 0.234449 | |
| 07:07.8 | 0.130268 | | | -0.44229 |
| 07:08.8 | 0.208238 | | | -0.15485 |
| 07:09.8 | 0.104074 | | 0.053479 | |
| 07:10.8 | 0.208179 | | | -0.23266 |
| 07:11.8 | 0.10422 | | | -0.88511 |
| 07:12.8 | | -0.10434 | | -0.85684 |
| 07:13.8 | | -0.0522 | | -0.90966 |
| 07:14.8 | | -0.18227 | | -0.28663 |
| 07:18.6 | | -0.07812 | 0.469413 | |
| 07:19.6 | | -0.07806 | | -0.15636 |
| 07:20.6 | | -0.28672 | | -0.66931 |
| 07:21.6 | 0.025501 | 0.025501 | 0.316702 | |
| 07:22.6 | | -0.02667 | 0.837776 | |
| 07:23.6 | | -0.07864 | 1.071618 | |
| 07:24.6 | | -0.23457 | 1.174439 | |
| 07:25.6 | | -0.33873 | 1.332917 | |
| 07:26.6 | | -0.18234 | 1.485449 | |
| 07:27.6 | | -0.23457 | 0.888185 | |
| 07:28.6 | | -0.26045 | 0.495224 | |
| 07:29.6 | | -0.41672 | | -0.56842 |
| 07:30.6 | | -0.18234 | | -0.57219 |
| 07:31.6 | 0.103442 | | | -0.7491 |
| AVERAGE | 0.346772 | -0.18677 | 0.677246 | -0.48375 |

FIG. 15

| TYPE OF BALANCE DYSFUNCTION | WEIGHT SIZE | COG VALUE FLUCTUATION | WEIGHT PLACEMENT POSITION |
|---|---|---|---|
| (CGx, CGy) | | | |

FIG. 18

| Wx | Wx_previous - Wx_current | CGx fluctuation | CGx Fluctuation (%) |
|---|---|---|---|
| -2.449769821 | | | |
| -1.01729156 | -1.432478261 | | |
| -0.208511509 | -0.808780051 | | |
| -0.078092072 | -0.130419437 | -2.371677749 | -2.329462708 |
| -0.15629156 | 0.078199488 | | |
| -0.547181586 | 0.390890026 | 0.469089514 | 0.460739884 |
| -0.07814578 | -0.469035806 | -0.469035806 | -0.460687131 |
| -0.156398977 | 0.078253197 | 0.078253197 | 0.076860317 |
| -0.026053708 | -0.130345269 | -0.130345269 | -0.128025168 |
| -0.286225064 | 0.260171355 | | |
| -0.286225064 | 0.078383632 | | |
| -0.599294118 | 0.234685422 | 0.573240409 | 0.563036929 |
| -0.521074169 | -0.078219949 | -0.078219949 | -0.076827661 |
| -0.83371867 | 0.312644501 | 0.312644501 | 0.307079538 |
| -0.520971867 | -0.312746803 | -0.312746803 | -0.307180019 |
| -0.598941176 | 0.077969309 | 0.077969309 | 0.076581483 |
| -0.494777494 | -0.104163683 | -0.104163683 | -0.102309605 |
| -0.598882353 | 0.104104859 | 0.104104859 | 0.102251829 |
| -0.494923274 | -0.103959079 | | |
| -0.286365729 | -0.208557545 | -0.312516624 | -0.306953937 |
| -0.338498721 | 0.052132992 | 0.052132992 | 0.051205043 |
| -0.208429668 | -0.130069054 | -0.130069054 | -0.12775387 |
| -0.31258312 | 0.104153453 | | |
| -0.312644501 | 6.13811E-05 | 0.104214834 | 0.102359846 |
| -0.10397954 | -0.208664962 | -0.208664962 | -0.204950798 |
| -0.416204604 | -0.208664962 | 0.312225064 | 0.306667566 |
| -0.416204604 | -0.052168798 | | |
| -0.312061381 | -0.051974425 | | |
| -0.156138107 | -0.155923274 | | |
| -0.051969309 | -0.104168798 | -0.364235294 | -0.357752032 |
| -0.208368286 | 0.156398977 | 0.156398977 | -0.230214196 |
| -0.156138107 | -0.052230179 | | |
| -0.130255754 | -0.025882353 | | |
| 0.026017903 | -0.156273657 | -0.234386189 | -0.230214196 |
| -0.208368286 | 0.234386189 | | |
| -0.49414578 | 0.285777494 | 0.520163683 | 0.51090495 |

FIG. 19

| Wy | Wy_previous - Wy_current | CGy fluctuation | CGy Fluctuation (%) |
|---|---|---|---|
| 2.345524297 | | | |
| 2.660608696 | -0.315084399 | | |
| 3.336184143 | -0.675575448 | -0.675575448 | |
| 2.342762148 | 0.993421995 | 0.993421995 | 0.975739428 |
| 3.412365729 | -1.069603581 | -1.069603581 | -1.050565008 |
| 3.204920716 | 0.207445013 | | |
| 2.969539642 | 0.235381074 | 0.235381074 | 0.231191373 |
| 3.753575448 | -0.784035806 | -0.784035806 | -0.77008024 |
| 3.491196931 | 0.262378517 | | |
| 2.523984655 | 0.967212276 | 0.967212276 | 0.949996233 |
| 2.968956522 | 0.262378517 | | |
| 3.56970844 | 0.967212276 | -1.045723785 | -1.027110265 |
| 3.230659847 | -0.444971867 | | |
| 2.683531969 | -0.600751918 | 0.886176471 | 0.870402837 |
| 3.360268542 | -0.676736573 | -0.676736573 | -0.664690897 |
| 3.072828645 | 0.287439898 | | |
| 2.864501279 | 0.208327366 | 0.495767263 | 0.486942778 |
| 3.150641944 | -0.286140665 | | |
| 3.803094629 | -0.652452685 | -0.93859335 | -0.921886714 |
| 3.774820972 | 0.028273657 | 0.028273657 | 0.027770396 |
| 3.827639386 | -0.052818414 | -0.052818414 | -0.051878265 |
| 3.204606138 | 0.623033248 | | |
| 2.448567775 | 0.756038363 | 1.379071611 | 1.354524615 |
| 3.074337596 | -0.625769821 | | |
| 3.587294118 | -0.512956522 | -1.138726343 | -1.118457409 |
| 2.601278772 | 0.986015345 | | |
| 2.080204604 | 0.521074169 | | |
| 1.846363171 | 0.233841432 | | |
| 1.743542199 | 0.102820972 | | |
| 1.585063939 | 0.158478261 | | |
| 1.432531969 | 0.152531969 | 2.154762148 | 2.11640813 |
| 2.029795396 | -0.597263427 | | |
| 2.422757033 | -0.392961637 | | |
| 3.486398977 | -1.063641944 | | |
| 3.490168798 | -0.003769821 | | |
| 3.667081841 | -0.176913043 | -2.234549872 | -2.19477566 |

FIG. 22

| Patient's weight | COG Coordinate | Weight size range | +CG_yfluctuation | | -CG_yfluctuation | | +CG_xfluctuation | | -CG_xfluctuation | |
|---|---|---|---|---|---|---|---|---|---|---|
| | (CGx, CGy) | 1st weight size to 2nd weight size | weight (%) | | weight (%) | | weight (%) | | weight (%) | |
| Largest | | | | | | | | | | |
| Second largest | | | | | | | | | | |
| Third largest | | | | | | | | | | |

FIG. 26

| Angle Range | | x1 | y1 | W_1 | W_1% | y1/x1 | C (If b/a>2, 0.3, 0.15) | x2 | y2 | W_2 | W_com | W_com% | %input (2.5%(2.8lb)) | Vest Position |
|---|---|---|---|---|---|---|---|---|---|---|---|---|---|---|
| 0 | 30 | | | | | | | | | | | | | |
| 30 | 60 | | | | | | | | | | | | | F |
| 60 | 90 | 0.0026 | 0.6294 | 1.72 | 24.81% | 245.2996882 | 0.3 | 0.001222994 | 0.3 | 0.92 | 0.90 | 28.86% | 0.81 | D |
| 90 | 120 | -0.0154 | 0.7492 | 2.04 | 29.53% | 48.7903976 | 0.3 | -0.006147743 | 0.3 | 0.82 | 1.23 | 39.35% | 1.10 | C |
| 120 | 150 | -0.1565 | 0.2608 | 0.83 | 11.99% | 1.666270473 | -0.15 | -0.15 | 0.249940571 | 0.80 | 0.03 | 1.10% | 0.03 | B |
| 150 | -180 | -0.2405 | 0.0115 | 0.66 | 9.49% | 0.047944409 | -0.15 | -0.15 | 0.007191601 | 0.41 | 0.25 | 7.93% | 0.22 | A |
| -180 | -150 | -0.3020 | -0.0216 | 0.83 | 11.93% | 0.071557476 | -0.15 | -0.15 | -0.010733621 | 0.41 | 0.42 | 13.35% | 0.37 | L |
| -150 | -120 | -0.2291 | -0.2099 | 0.85 | 12.25% | 0.916098932 | -0.15 | -0.15 | -0.13741484 | 0.56 | 0.29 | 9.40% | 0.26 | K |
| -120 | -90 | | | | | | | | | | | | | J |
| -90 | -60 | | | | | | | | | | | | | I |
| -60 | -30 | | | | | | | | | | | | | H |
| -30 | 0 | | | | | | | | | | | | | G |
| total | | | | 6.923524 | | | | | | 3.808304961 | 3.115218602 | | 2.8 | |

FIG. 27

FRONT

| $G_1$ | $G_2$ | $G_3$ |
|---|---|---|
| $H_1$ | | |
| $I_1$ | | |
| $J_1$ | | |
| $K_1$ | | 0.37 0.26 |
| $L_1$ | $L_2$ | |

BACK

| $A_1$ | $A_2$ | 0.22 |
|---|---|---|
| $B_1$ | | 0.03 |
| $C_1$ | | 1.10 |
| $D_1$ | | 0.81 |
| $E_1$ | | |
| $F_1$ | $F_2$ | $F_3$ |

BALANCE COMPENSATING DEVICE, BODY CENTER MEASURING APPARATUS, BALANCE COMPENSATION SYSTEM, AND BALANCE COMPENSATION METHOD

CROSS-REFERENCE TO RELATED APPLICATIONS

This application is a Continuation application of U.S. patent application Ser. No. 16/443,339, filed on Jun. 17, 2019, which is a continuation of U.S. patent application Ser. No. 16/380,881, filed on Apr. 10, 2019 which claims the benefit of Korean Priority Patent Application KR 10-2018-0041774, filed on Apr. 10, 2018, Korean Priority Patent Application KR 10-2018-0156318, filed on Dec. 6, 2018, and Korean Priority Patent Application KR 10-2019-0034851, filed on Mar. 27, 2019. The content of each of the above applications is hereby incorporated by reference.

BACKGROUND

Many people with neurological and balance disorders have problems in maintaining their body balance. For example, many people with balance disorders caused by Parkinson's disease, ataxia, multiple sclerosis, accidents, stroke, degeneration of visual/vestibular/proprioception systems or the like could have a range of difficulties in carrying out simple daily activities such standing or walking.

U.S. Pat. No. 7,708,673 describes methods and devices for providing a patient having a balance disorder, or proprioceptive loss, with a weighted garment or orthotic device (hereinafter referred to as "BV") tending to improve the patient's balance by aligning a patient's Center of Gravity (COG) over their base of support biomechanically or proprioceptively (e.g., by receiving stimuli originating in muscles, tendons, and other internal tissues). The "BV" resulted in improving the patients with balance disorders in various levels.

However, the BV according to the related art has a number of limitations and problems. For example, a BV customized for a patient is made after various tests such as perturbation tests performed on the patient. In addition, as the tests are carried out by trained physical therapists or medical professionals (trained specifically for measuring and fitting the weights needed in the BV), the patient is unable to obtain the BV without visiting trained physical therapists or medical professionals. Therefore, it is often cumbersome and time consuming for the patients who would have to travel long distances and undergo various tests for a long time.

Furthermore, since the size and the placement position of the weights attached to the BV often determines the degree of improvement, the effectiveness of the BV are determined by the experience and skills of the physical therapists or medical professionals, as they use their skills gained through their training and experience to carry out the tests and determine the strategic placements of the weights.

Many patients with balance disorders such as Parkinson's disease or ataxia have tremors in one or more parts of the body, and such tremors often cause headaches or double vision, thereby hindering these patients from carrying out normal daily activities.

BRIEF SUMMARY

According to an aspect of the present disclosure, it is possible to provide a balance compensating device capable of compensating for balance of people having a balance dysfunction and a body center measuring apparatus, a balance compensation system, and balance compensation methods which enable ordinary persons to make a balance compensating device capable of compensating for balance of people having a balance dysfunction.

According to an aspect of the present disclosure, it is possible to provide a tremor compensating device capable of reducing a tremor of people having tremors in one or more parts of the body and a tremor measuring apparatus, a tremor compensation system, and tremor compensation methods which enable ordinary persons to make a balance compensating device capable of reducing tremors of people having tremors in one or more parts of the body.

BRIEF DESCRIPTION OF THE DRAWINGS

FIG. 12 is a diagram illustrating log data indicating a result of measuring a COG value of a patient A having ataxia in units of one second according to the present disclosure;

FIG. 13 is a diagram illustrating a data indicating a weight size obtained by converting a COG value (CGx, CGy) calculated by a COG value calculating unit into a weight according to the present disclosure;

FIG. 14 is data illustrating a COG value (CGx, CGy) fluctuation calculated by a COG value fluctuation calculating unit according to the present disclosure;

FIG. 15 is a diagram illustrating balance compensation history information stored in a database (DB) according to the present disclosure;

FIG. 18 is a diagram illustrating a method of calculating a COG value (CGx) fluctuation using a Wx value in FIG. 13 according to the present disclosure;

FIG. 19 is a diagram illustrating a method for calculating a COG value (CGy) fluctuation using a Wy value in FIG. 13 according to the present disclosure;

FIG. 22 is a diagram illustrating a table stored as a result of executing a recorder function of a balance compensation program according to the present disclosure;

FIG. 26 is a table for describing a method of determining weight sizes and weight placement positions using COG values illustrated in FIG. 25 according to the present disclosure;

FIG. 27 is a diagram illustrating an example in which weight sizes and weight placement positions determined as described above are shown in the drawings shown in FIGS. 7 and 8 according to the present disclosure.

DETAILED DESCRIPTION

Figure 1:
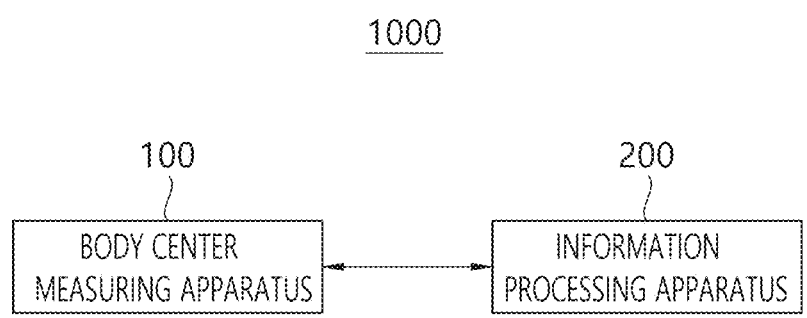
FIG. 1 is a block diagram illustrating a balance compensation system according to the present disclosure.

Hereinafter, a balance (tremor) compensating device, a body center (tremor) measuring apparatus, a balance (tremor) compensation system, and a balance (tremor) compensation method according to an embodiment of the present disclosure will be described with reference to the appended drawings. It is to be understood, however, that the following explanation is merely exemplary in describing the devices and methods of the present disclosure. Accordingly, any number of reasonable and foreseeable modifications, changes, and/or substitutions are contemplated without departing from the spirit and scope of the present disclosure.

A balance compensating vest may include a balance compensating device for compensating for balance of people having a balance dysfunction caused by balance disorders such as Parkinson's disease, ataxia, multiple sclerosis, accidents, stroke, degeneration of visual/vestibular/proprioception systems or the like but this is merely an example, and the present disclosure is not limited thereto.

The balance compensating device for compensating for the balance of people having a balance dysfunction is applicable to any device which can be attached to a patient's body or worn by a patient such as a wearable device such as a garment, an orthotic, or a brace. For example, a balance compensating device can be made with plastic materials with weights strategically placed and imprinted using a 3D printer.

Further, in the present disclosure, a tremor compensating vest will be described as an example of a device for reducing tremors of a patient in one or more parts of the body, but this is merely an example, and the present disclosure is not limited thereto.

In this specification, a term "tremor" includes involuntary muscle contraction and relaxation involving oscillations or twitching movements of one or more parts of the body or unintentional trembling or shaking movements in one or more parts of the body.

The balance compensating devices, the body center measuring apparatus, the balance compensation system, and the balance compensation methods (which may be referred to collectively as "balance compensation functionality") may or may not be the tremor compensating devices, the tremor measuring apparatus, the tremor compensation system, and the tremor compensation methods (hereinafter, collectively a "tremor compensation functionality"). A balance compensation functionality and a tremor compensation functionality can be implemented by a single device/apparatus/system/method, or they can be implemented by separate devices/apparatus/systems/methods.

The present disclosure describes a balance compensating functionality, and a tremor compensating functionality, but for the sake of convenience, the description of the present disclosure will focus on the balance compensation functionality. The description applied for a balance compensation functionality can be applied to describe a tremor compensating functionality.

Further, in the present disclosure, a weight will be described as an object or a stimulus for compensating balance and/or a tremor of a patient, but this is merely an example, and an object or a stimulus for compensating balance and a tremor of a patient is not limited to a specific object or stimulus as long as it can be used for compensating balance and/or a tremor of a patient.

In the present disclosure, the term "compensate" may be used interchangeably with the term "correct", and both terms include improving or reducing a balance dysfunction or a tremor of a patient.

FIG. 1 is a block diagram illustrating a balance compensation system 1000 according to the present disclosure. The balance compensation system 1000 of the present disclosure includes a body center measuring apparatus 100 and an information processing apparatus 200 as illustrated in FIG. 1.

The body center measuring apparatus 100 is an apparatus that measures patient information such as the body center of a patient, and the information processing apparatus 200 is an apparatus that performs a process of displaying patient information such as the body center of the patient using a measurement signal or a measurement value output from the body center measuring apparatus 100 on a coordinate system, a process of determining a size and a placement position of a weight attached to a balance compensating vest using the measurement signal or the measurement value, and a process of measuring and displaying a tremor of the patient using the patient information. Thus, the body center measuring apparatus 100 may also be referred to as a tremor measuring apparatus. In this sense, the balance compensation system 1000 may also be referred to as a tremor compensation system.

Here, measuring the body center of the patient by the body center measuring apparatus 100 includes outputting signals by which it can be understood whether or not the body center of the patient is in a normal position and includes displaying measurement values measured by sensors through a display device so that it can be understood whether or not the body center of the patient is in a normal position or displaying the body center of the patient through a coordinate system (for example, FIG. 6) to be described later using the measurement signals or the measurement values.

The body center of the patient indicates the center of the body at which the patient's posture is maintained when the patient is standing, walking, or running, and, in the present disclosure, the body's center of gravity (COG) is described as an example of the body center of the patient, but the body center of the patient is not limited to the COG, and information such as, for example, a center of pressure (COP) or a center of mass (COM) may be used.

The body center measuring apparatus 100 has, for example, a scale capable of measuring a body weight of a patient. However, the body center measuring apparatus 100 of the present disclosure is not limited to a scale and is not limited to a specific form as long as the body center of the patient can be measured.

To facilitate understanding of the present disclosure, the body center measuring apparatus 100 employing the scale will be described as an example.

Figure 2:
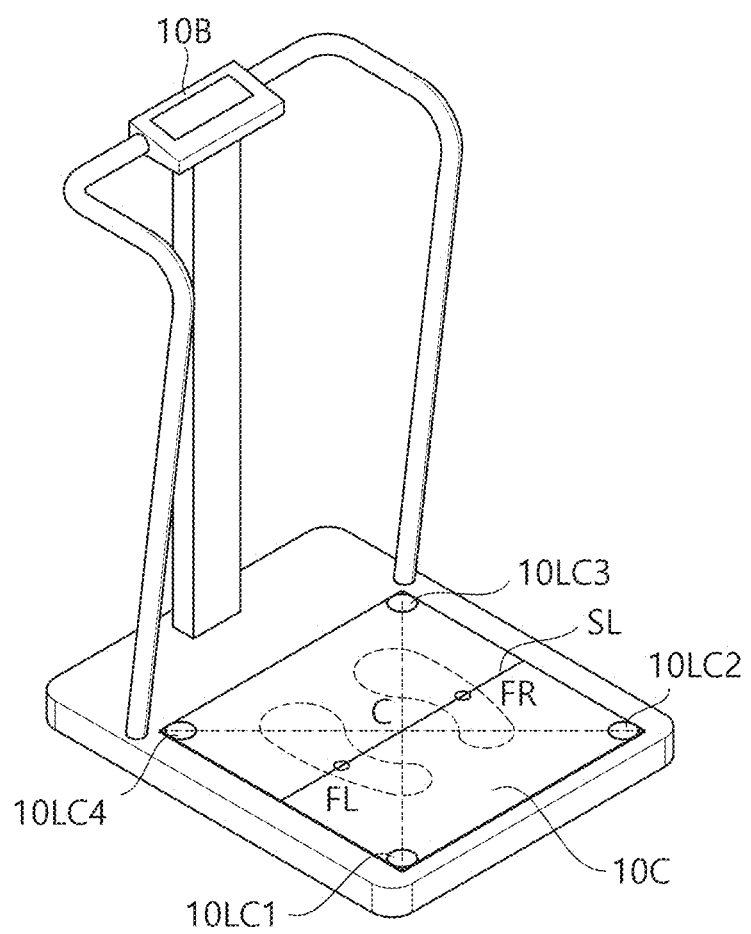
FIG. 2 is a diagram illustrating a body center measuring apparatus according to the present disclosure.
Figure 3:
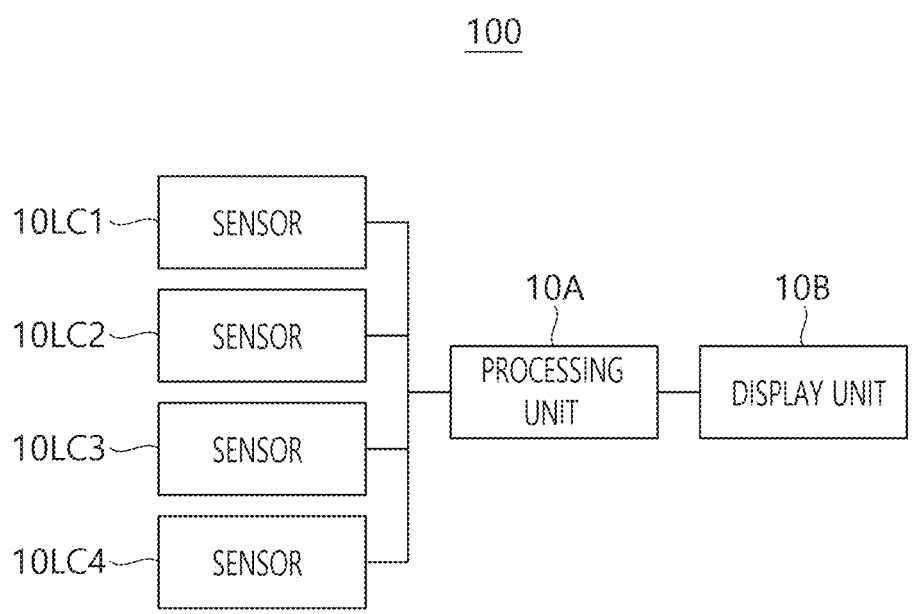
FIG. 3 is a block diagram illustrating a configuration of a body center measuring apparatus according to the present disclosure.

FIG. 2 is a diagram illustrating the body center measuring apparatus 100 according to the present disclosure, and FIG. 3 is a block diagram illustrating a configuration of the body center measuring apparatus 100 according to the present disclosure.

As illustrated in FIGS. 2 and 3, the body center measuring apparatus 100 includes a plurality of sensors 10LC1, 10LC2, 10LC3, and 10LC4, a processing unit 10A that processes measurement signals of the sensors 10LC1, 10LC2, 10LC3, and 10LC4, a display unit 10B that displays measurement values obtained by performing a predetermined process through the processing unit 10A, and a platform 10C below which the plurality of sensors 10LC1, 10LC2, 10LC3, and 10LC4 are arranged and on which the patient stands.

Each of the sensors 10LC1, 10LC2, 10LC3, and 10LC4 includes, for example, a load cell, and measures a weight applied thereof and outputs the measurement signal.

In the present embodiment, the body center is measured using four load cells, but the number of sensors is not limited to four, and the number of sensors is not particularly limited as long as the body center can be measured.

In the present embodiment, the example in which the load cell is used is described, but a type of sensor is not particularly limited. For example, a force plate may be employed. In the case of the force plate, the center of pressure (COP) indicates the body center.

The processing unit 10A performs a process such as signal amplification or digital conversion on the measurement signals of the sensors 10LC1, 10LC2, 10LC3, and 10LC4 and outputs the processed signals to the display unit 10B or the information processing apparatus 200.

The display unit 10B displays the measurement signals or the measurement values of the sensors 10LC1, 10LC2, 10LC3, and 10LC4.

Hereinafter, the measurement values displayed on the display unit 10B indicating the measurement signals of the sensors 10LC1, 10LC2, 10LC3, and 10LC4 are referred to as LC1, LC2, LC3, and LC4.

When a normal person (e.g., a person without balance dysfunction) stands at one position for a few seconds, the body may sway or move back and forth slightly. Therefore, the patient may sway or move back and forth similarly to the normal person, and in this case, the body center fluctuates. To acquire more accurate measurement values, a filter process may be performed to obtain measurement values LC1, LC2, LC3, and LC4. A process of acquiring the measurement values LC1, LC2, LC3 twice or more and averaging them may be an example of a filter process. The measurement values LC1, LC2, LC3, and LC4 may be obtained by applying a predetermined error range or a predetermined threshold value to the measurement signals of the sensors 10LC1, 10LC2, 10LC3, and 10LC4.

The platform 10C is a plate on which the patient stands for body center measurement. "C" in the platform 10C indicates a position indicating the center of the platform 10C itself that may also be a COG of the platform 10C itself, and is a point coinciding with the COG of the normal person when the normal person having no balance dysfunction stands on the platform 10C.

The platform 10C may have a shape capable of enabling a load to be equally distributed to the sensors 10LC1, 10LC2, 10LC3, and 10LC4 when a person stands thereon. Preferably, the platform 10C has a square shape. In this case, the sensors 10LC1, 10LC2, 10LC3, and 10LC4 may be installed at the same distance from the "C" of the platform 10C.

The platform 10C may have a shape other than a square shape, and in this case, preferably, the sensors 10LC1, 10LC2, 10LC3, and 10LC4 are installed at the same distance from the center "C" of the platform 10C so that the load of the patient is evenly applied to the sensors 10LC1, 10LC2, 10LC3, and 10LC4.

However, the platform is not limited to such a shape and shapes with unequal load distribution may also be used. When the shape of the platform and location of the sensors provides for an unequal distribution, a transform may be applied to the measurement signals to normalize them for further processing.

The platform 10C includes indications of positions (FL, FR) corresponding to COGs of both feet on which the patient should stand. When the normal person having no balance dysfunction stands such that the COGs of both feet coincide with the positions (FL, FR), the COG of the platform 10C and the COG of the normal person coincide with each other.

The position FL is a middle position of a line segment connecting a middle position between "C" and the sensor 10LC4 with a middle position between "C" and the sensor 10LC1, and the position FR is a middle position of a line segment connecting a middle position between "C" and the sensor 10LC3 with a middle position between "C" and the sensor 10LC2, and if the platform 10C is cut in half by an imaginary line passing through "C" while being perpendicular to a line SL to be described later, the position (FL) and the position (FR) are positions corresponding to COGs of the halves of the platform 10C.

To measure the COG of the patient accurately, the patient preferably stands on the positions (FL, FR) so that the load of the patient is evenly applied to the sensors 10LC1, 10LC2, 10LC3, and 10LC4.

The line SL passing through "C" while dividing the platform 10C in half may be indicated for alignment. A part of the foot corresponding to the COG when viewed from side could correspond to the patient's malleolar zone, and when the line SL is indicated, it is possible to easily see whether or not the patient stands on the positions (FL, FR) correctly by determining whether or not the line SL aligns with the malleolar zone of the foot.

Figure 4:
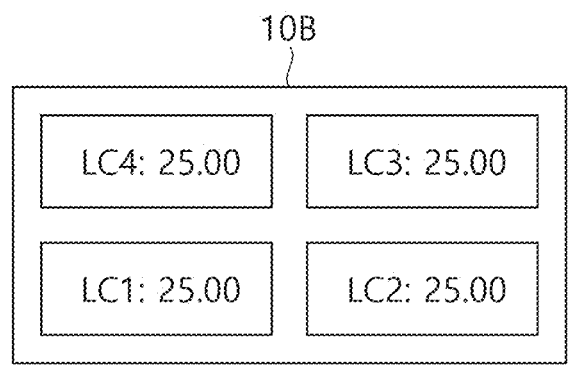
FIG. 4 is a diagram illustrating an example of a display unit that displays measurement values of sensors according to the present disclosure.

FIG. 4 is a diagram illustrating the display unit 10B that displays the measurement values (LC1, LC2, LC3, and LC4 of the sensors 10LC1, 10LC2, 10LC3, and 10LC4 when the normal person with a body weight of 100 pounds stands on the platform 100C of the body center measuring apparatus 100.

As illustrated in FIG. 4, the display unit 10B displays the measurement values LC1, LC2, LC3, and LC4 of the sensors 10LC1, 10LC2, 10LC3, and 10LC4, respectively. Further, the display unit 10B may display the sum of the measurement values LC1, LC2, LC3, and LC4 of the sensors 10LC1, 10LC2, 10LC3, and 10LC4.

Since the measurement values LC1, LC2, LC3 and LC4 of the sensors 10LC1, 10LC2, 10LC3, and 10LC4 are respectively displayed, the COG of the person standing on the platform 100C of the body center measuring apparatus 100 can be recognized as deviating from a normal COG when the measurement values LC1, LC2, LC3 and LC4 of the sensors 10LC1, 10LC2, 10LC3, and 10LC4 are not equal to one another.

Further, when the patient having the balance dysfunction is standing on the platform 100C, with a stimulus object, (e.g., a weight is attached on the balance compensating vest that the patient is wearing), it is understood that the COG of the patient is corrected to the normal COG through the balance compensating vest if the measurement values LC1, LC2, LC3, and LC3 of the sensors 10LC1, 10LC2, 10LC3, and LC4 are all equal to one another. It is possible to compensate for the COG of the patient easily through the body center measuring apparatus 100 without the help of the information processing apparatus 200. A further detailed operation will be described later.

Figure 6:
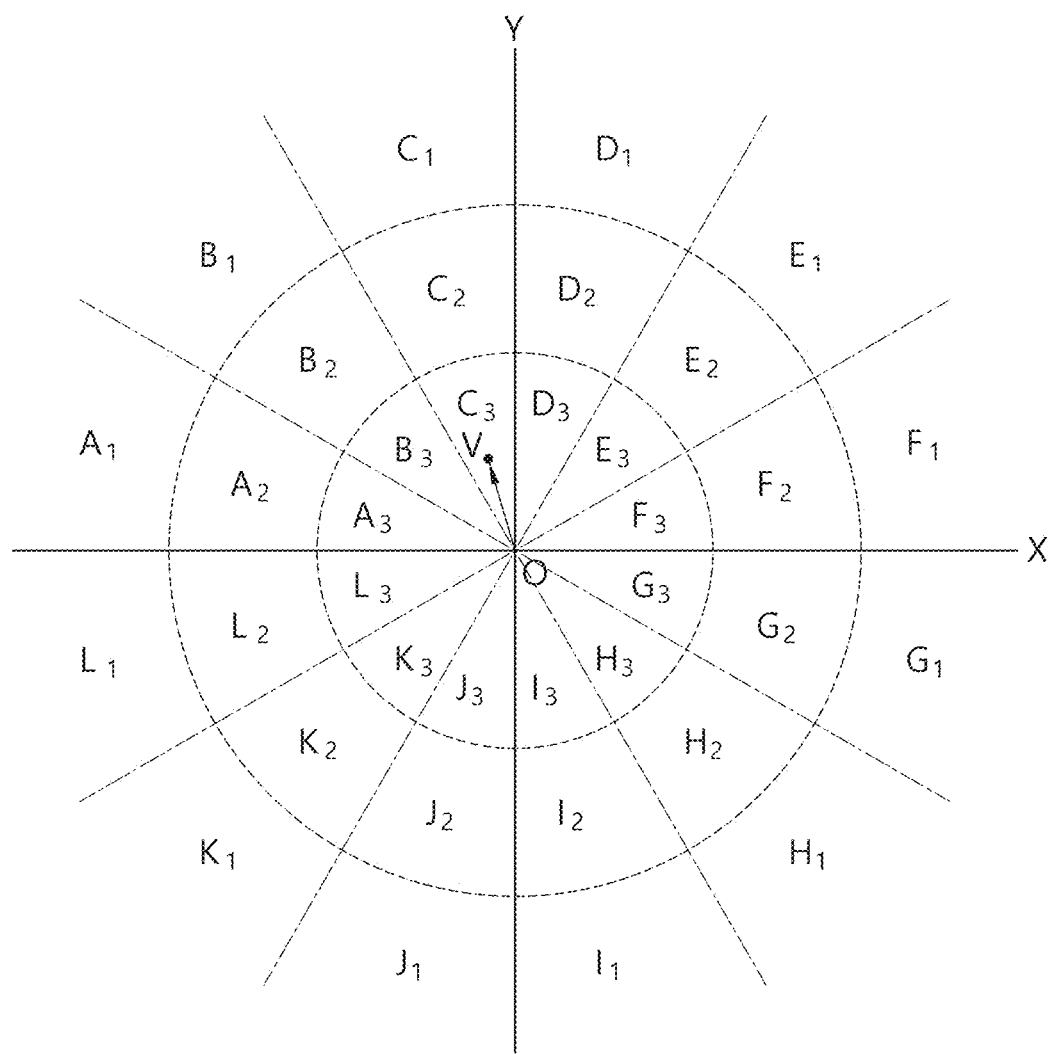
FIG. 6 is a diagram illustrating an example in which a processing unit calculates a center of gravity (COG) of a patient and displays the COG of the patient on a display unit according to the present disclosure.

The display unit 10B may be configured to display a coordinate system indicating the COG of the patient as illustrated in FIG. 6.

The body center measuring apparatus 100 may include a height adjustment mechanism for adjusting the height of each sensor of the platform 100C and a leveling mechanism for indicating a level state of the platform 10C, indicating whether or not the sensors 10LC1, 10LC2, 10LC3, and 10LC4 of the platform 100C are at the equal level so that the equal load is applied to the sensors 10LC1, 10LC2, 10LC3, and 10LC4 of the platform 100C. Preferably, the number of height adjustment mechanisms to be installed corresponds to the number of sensors, and the respective height adjustment mechanisms can be individually adjusted so that the level of the platform 100C is adjusted. As the leveling mechanism, a digital level or a water level or other leveling sensors may be used.

Figure 5:
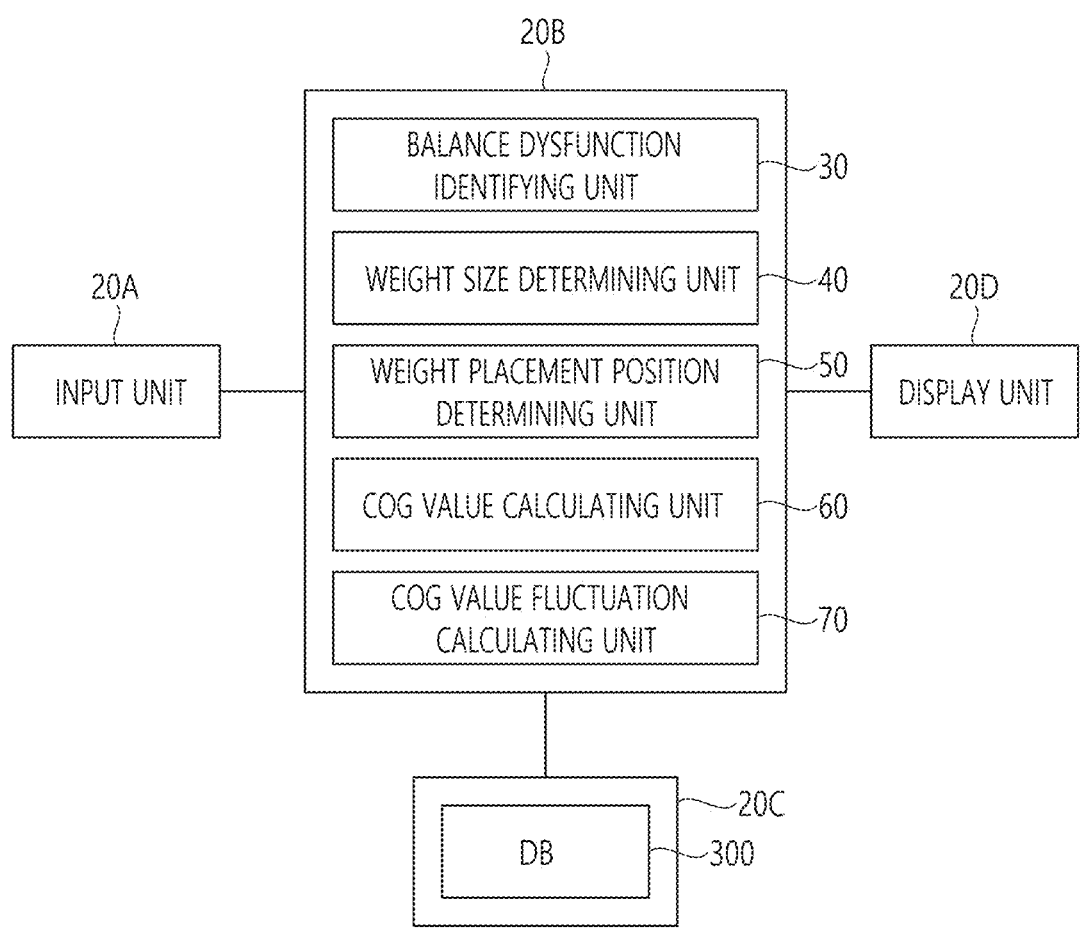
FIG. 5 is a block diagram illustrating a configuration of an information processing apparatus according to the present disclosure.

FIG. 5 is a block diagram illustrating a configuration of the information processing apparatus 200. The information processing apparatus 200 is, for example, a smart phone, a personal computer (PC), or a dedicated terminal for balance compensation. The information processing apparatus 200 includes an input unit 20A, a processing unit 20B, a storage unit 20C, and a display unit 20D.

The input unit 20A receives the measurement signals or the measurement values LC1, LC2, LC3, and LC4 from the body center measuring apparatus 100 and provides the measurement signals or the measurement values LC1, LC2, LC3, and LC4 to the processing unit 20B. The input unit 20A includes a communication interface and may be a wired interface such as USB or HDMI or a wireless interface such as Bluetooth. The body center measuring apparatus 100C and the information processing apparatus 200 can be connected via wired or wireless communication.

The storage unit 20C has a database 300 that stores the measurement signal or the measurement values LC1, LC2, LC3, and LC4 received from the input unit 20A and stores balance compensation history information of patients. The balance compensation history information includes a body center value (for example, a COG value (CGx, CGy)) (for example, an average value), a balance dysfunction type, a weight size, a body center (COG) value fluctuation, a placement position, and the like. Hereinafter, the COG value will be described as an example of the body center value for the sake of convenience of description.

The processing unit 20B receives the measurement signals or the measurement values LC1, LC2, LC3, and LC4 from the input unit 20A. When the measurement signals are received, the processing unit 20B calculates the measurement values LC1, LC2, LC3, and LC4. The processing unit 20B calculates the COG value (CGx, CGy) of the patient from the measurement values LC1, LC2, LC3, and LC4, and causes the COG value (CGx, CGy) to be displayed on a COG coordinate system (XY coordinates). Further, the processing unit 20B calculates a size of weight (e.g., a stimulus) to be described later using the COG values (CGx, CGy) calculated from the measurement values (LC1, LC2, LC3, LC4) and causes the weight size to be displayed on the display unit 20D. Further, the processing unit 20B calculates the COG value fluctuation using the COG values (CGx, CGy) and causes the COG value fluctuation to be displayed on the display unit 20D. Further, the processing unit 20B calculates a weight placement position on the balance compensating vest using the COG values (CGx, CGy) and/or the COG value fluctuation and causes the weight placement position to be displayed on the display unit 20D. The processes of the processing unit 20B may be performed by software. A further detailed operation of the processing unit 20B will be described hereinafter.

The balance dysfunctions of the patients can be roughly classified into eight types: (1) an anterior balance dysfunction; (2) a posterior balance dysfunction; (3) a lateral-left balance dysfunction; (4) a lateral-right balance dysfunction; (5) an anterior lateral-left balance dysfunction; (6) an anterior lateral-right balance dysfunction; (7) a posterior lateral-left balance dysfunction; and (8) a posterior lateral-right balance dysfunction.

The anterior balance dysfunction refers to a patient's condition that the patient loses balance in the anterior direction, and the posterior balance dysfunction refers to a condition that the patient loses balance in a posterior direction. The lateral-left balance dysfunction refers to a condition that the patient loses balance in a left direction, and the lateral-right balance dysfunction refers to a condition that the patient loses balance in the right direction. The anterior lateral-left balance dysfunction refers to a condition that the patient loses balance in the anterior left direction, the anterior lateral-right balance dysfunction refers to a condition that the patient loses balance in the anterior right direction, the posterior lateral-left balance dysfunction refers to a condition that the patient loses balance in the posterior left direction, the posterior lateral-right balance dysfunction refers to a condition that the patient loses balance in the posterior right direction.

In the related art, the physical therapist identifies the type of the balance dysfunction by conducting a perturbation test (the physical therapist pushes or pulls the shoulders of the patient forward, backward, left, and right).

However, in the present disclosure, when the patient is standing on the platform 10C of the body center measuring apparatus 100, the measurement values LC1, LC2, LC3, and LC4 are displayed on the display unit 10B, so that the type of balance dysfunction can be identified on the basis of a relation of the measurement values LC1, LC2, LC3, and LC4.

In the present embodiment, the patient stands towards the display unit 10B in FIG. 2, the left foot of the patient is at the position FL close to the sensors 10LC1 and 10LC4, and the right foot of the patient is at the position FR close to the sensors 10LC2 and 10LC3. Under this assumption, a method for identifying the balance dysfunction will be described. However, it will be appreciated that this orientation is exemplary and illustrative and other orientations may also be used.

According to one embodiment of the present disclosure, a balance dysfunction identifying method to be described hereinafter may be performed by a person (hereinafter an "operator"), and it is possible for an operator to identify a balance dysfunction from the data gathered from using the body center measuring apparatus 100 only. According to another embodiment of the present disclosure, the identification of the balance dysfunction is performed by the information process apparatus 200 connected to the body center measured apparatus 100 in a wired or wireless manner, based on the measurement values LC1, LC2, LC3, LC4 (e.g., the COG value (CGx, CGy)).

The patients having balance dysfunction have at least one of the following balance dysfunctions:

The anterior balance dysfunction is identified when the measurement value LC4 has the same value as the measurement value LC3, the measurement value LC1 has the same value as the measurement value LC2, and a value of LC4+LC3 is greater than a value of LC1+LC2 (the COG of the patient is located on the +Y axis in the coordinate system to be described later, e.g., the COG value is (0, +CGy)) (Here, CGx indicates a COG value of the patient on the X-axis, CGy indicates a COG value of the patient on the Y-axis, and signs of "+" or "−" indicate whether CGx or CGy has a negative or positive value).

The posterior balance dysfunction is identified when the measurement value LC4 has the same value as the measurement value LC3, the measurement value LC1 has the same value as the measurement value LC2, and a value of LC1+LC2 is greater than a value of LC4+LC3 (the COG of the patient is located on the −Y-axis in the coordinate system. The COG value is (0, −CGy)).

The lateral-left balance dysfunction is identified when the measurement value LC4 has the same value as the measurement value LC1, the measurement value LC3 has the same value as the measurement value LC2, and a value of LC4+LC1 is greater than a value of LC3+LC2 (e.g., the COG of the patient is located on the −X axis in the coordinate system. The COG value is (−CGx, 0)).

The lateral-right balance dysfunction is identified when the measurement value LC4 has the same value as the measurement value LC1, the measurement value LC3 has the same value as the measurement value LC2, and a value of LC3+LC2 is larger than a value of LC4+LC1 (e.g., the COG of the patient is located on the +X axis in the coordinate system described later. The COG value is (+CGx, 0)).

The anterior lateral-left balance dysfunction is identified when the measurement value LC4 has the largest value, and the measurement value LC2 has the smallest value (the COG of the patient is located on the −X+Y plane in the coordinate system. In this example, the COG value is (−CGx, +CGy)).

The anterior lateral-right balance dysfunction is identified when the measurement value LC3 has the largest value, and the measurement value LC1 has the smallest value (e.g., the COG of the patient is located on the +X+Y plane in the coordinate system. In this example, the COG value is (+CGx, +CGy)).

The posterior lateral-left balance dysfunction is identified when the measurement value LC1 has the largest value, and the measurement value LC3 has the smallest value (e.g., the COG of the patient is located on the −X −Y plane in the coordinate system. In this example, the COG value is (−CGx, −CGy)).

The posterior lateral-right balance dysfunction is identified when the measurement value LC2 has the largest value, and the measurement value LC4 has the smallest value (e.g., the COG of the patient is located on the +X −Y plane in the coordinate system. In this example, the COG value is (+CGx, −CGy)).

The operator can identify the balance dysfunction using the balance dysfunction identifying method described above while viewing the display unit 10B of the body center measuring apparatus 100 or the display unit 20D of the information processing apparatus 200. The balance dysfunction identifying method may be implemented by the processing unit 20B which can be in the form of hardware or software.

It will be appreciated that a same value can, but does not require, the same numeric value. A threshold or deadband may also be applied to determine when measurements are close enough that they are considered the same for the purposes of the above processing.

The processing unit 20B includes a balance dysfunction identifying unit 30, a weight size determining unit 40, a weight placement position determining unit 50, and a COG value calculating unit 60.

The COG value calculating unit 60 is a body center value calculating unit that calculates a body center value and that calculates the COG value (CGx, CGy) using the measurement values LC1, LC2, LC3, and LC4. The COG value (CGx, CGy) can be calculated by the following Formula (1).

$$CGx=(LC1\times X1+LC2\times X2+LC3\times X3+LC4\times X4)/(LC1+LC2+LC3+LC4)$$

$$CGy=(LC1\times Y1+LC2\times Y2+LC3\times Y3+LC4\times Y4)/(LC1+LC2+LC3+LC4) \quad (1)$$

Here, LC1, LC2, LC3, and LC4 indicate the measurement values, and X1, X2, X3, and X4 indicate X axis positions (lengths) of the sensors from the origin. Y1, Y2, Y3, and Y4 indicate Y-axis positions (lengths) of the sensors from the origin.

FIG. 12 is a table illustrating log data indicating a result of measuring the COG value of the patient A having ataxia in units of one second. The log data in FIG. 12 is data in which values outside a predetermined error range are excluded from original log data. For example, log data having an abnormally large value or an abnormally small value is determined as an error and is excluded from original log data.

In FIG. 12, the COG value is measured in units of one second, but the COG value can be measured in less than one seconds such as in units of 0.5 seconds or in units of 0.1 seconds. For example, the COG value fluctuation can be measured more accurately when the COG value is measured at intervals of 0.1 sec.

The log data of FIG. 12 is a measurement result obtained by the body center measuring apparatus 100 including the platform 10C having a size of 19.55 inches×19.55 inches with reference to the positions of the sensors located below the platform 10C.

In the following description, the data used in FIG. 12 and subsequent drawings (FIG. 13 & FIG. 14) are data measured from patient A who has ataxia using the body center measuring apparatus 100 including the platform 10C having the size of 19.55 inches×19.55 inches.

The balance dysfunction identifying unit 30 identifies the balance dysfunction of the patient based on the COG value (CGx, CGy) calculated by the COG value calculating unit 60. The type of the balance dysfunction of the patient can be identified based on the sign (+, −) of the calculated COG values (CGx, CGy), and the calculated COG value, may be, for example, the average COG value.

The weight size determining unit 40 determines the weight size based on the COG value (CGx, CGy) calculated by the COG value calculating unit 60. For example, the weight size is determined by converting the COG value (CGx, CGy) calculated by the COG value calculating unit 60 into a weight. For example, a weight (Wx) of CGx and a weight (Wy) of CGy are calculated by multiplying the calculated COG value (CGx, CGy) by a weight per unit (for example, a weight per inch) of the COG value using the following Formula (2), and the weight size is decided using Wx and Wy.

$$Wx = Wtotal/2/Lx \times CGx$$

$$Wy = Wtotal/2/Ly \times CGy \qquad (2)$$

Here, Wtotal indicates the body weight of the patient, Lx indicates the length of the platform in a transverse direction (an X-axis direction), and Ly indicates the length of the platform in a longitudinal direction (a Y-axis direction).

FIG. 13 illustrates data indicating the weight size obtained by converting the COG value (CGx, CGy) calculated by the COG value calculating unit 60 into a weight. In FIG. 13, Wx indicates a weight size corresponding to CGx and indicates a degree of deviation (in weight size) of the COG of the patient from the original in the X-axis direction (the lateral direction). Wy indicates the weight size corresponding to CGy and indicates a degree of deviation (in weight size) of the COG of the patient from the original in the Y-axis direction (the anteroposterior direction). W1 is obtained by a square root value ($\sqrt{(Wx^2+Wy^2)}$) of a sum of Wx squared and Wy squared and indicates a first weight size. W2 is obtained by a sum of Wx and Wy and indicates a second weight size. When each of Wx and Wy has a value of 0, it indicates a COG measurement of a normal person.

The weight size determining unit 40 determines the weight size of the weight (e.g., stimulus) to be attached to the balance compensating vest. Preferably, the weight size determining unit 40 determines a range of the first weight size W1 to the second weight size W2 and displays the weight size range as the weight size. The weight size determining unit 40 may determine a range of the first weight size W1 to the second weight size W2 based on an average of the COG values (CGx, CGy) measured for a predetermined time.

In the case of the patient A, it is determined that the COG deviates by 0.39 pounds in the left (−X axis) direction and 2.91 pounds in the forward (+Y axis) direction as compared with the COG of the normal person. Thus, when the weight with the range of 2.97 pounds (the first weight size) to 3.31 pounds (the second weight size) is attached to the balance compensating vest, the COG of the patient A can be corrected to the COG of the normal person.

The weight placement position determining unit 50 determines the position of the balance compensating vest to which the weight (stimulus) is to be attached based on the COG value (CGx, CGy) calculated by the COG value calculating unit 60. For example, as the origin in FIG. 6 represents the COG value of a normal person, the COG value (CGx, CGy) of the patient calculated by the COG value calculating unit 60 can be indicated using a vector V including an imaginary line extending from the origin to the COG value (CGx, CGy) of the patient, and the position on the balance compensating vest to which the weight is to be placed is determined based on a length and a direction of a vector V.

A method of determining the position on the balance compensating vest to which the weight is to be attached will be described hereinafter.

The functions of the balance dysfunction identifying unit 30, the weight size determining unit 40, the weight placement position determining unit 50, and the COG value calculating unit 60 of the processing unit 20B may be implemented, for example, by readings a balance compensation program from the storage unit 20C and executing the balance compensation program through a central processing device (CPU).

FIG. 6 is a diagram illustrating an example of calculating the COG value of the processing unit 20B and displaying the calculated COG value on the display unit 20D. Referring to FIG. 6, the XY coordinate system is a COG coordinate system corresponding to a human body. The X-axis corresponds to the frontal axis (frontal plane of a human body), and the Y-axis corresponds to the sagittal axis (sagittal plane of a human body).

In FIG. 6, the origin O indicates the COG of the normal person having no balance dysfunction. When the measurement values LC1, LC2, LC3, and LC4 are substantially equal to one another, the COG of the normal person is located at the origin O. The balance dysfunction identifying unit 30 of the processing unit 20B identifies at least one of the balance dysfunctions of the patient described above using the balance dysfunction identifying method described above.

The balance dysfunction identifying unit 30 of the processing unit 20B identifies the anterior balance dysfunction when the COG of the patient is located on the +Y axis; identifies the posterior balance dysfunction when the COG of the patient is located on the −Y axis; identifies the lateral-left balance dysfunction when the COG of the patient is located on the −X axis; identifies the lateral-right balance dysfunction when the COG of the patient is located on the +X axis; identifies the anterior lateral-left balance dysfunction when the COG of the patient is located on the −X+Y plane; identifies the anterior lateral-right balance dysfunction when the COG of the patient is located on the +X+Y plane; identifies the posterior lateral-left balance dysfunction when the COG of the patient is located on the −X−Y plane; and identifies the posterior lateral-right balance dysfunction when the COG of the patient is located on the +X−Y plane. In the XY coordinate system of FIG. 6, the signs of "−" such as −X or −Y is used to distinguish the posterior from the anterior or distinguish the left from the right.

The balance dysfunction can be indicated by a vector V in the COG coordinate system of the patient in an XY coordinate system. A direction of the vector V in the XY coordinate system corresponds to the type of balance dysfunction, and the length of the vector V corresponds to the weight size of the stimulus. The placement position of the weight (stimulus) is determined by the location of the vector V in the XY coordinate system.

In the COG coordinate system illustrated in FIG. 6, each of the balance dysfunctions (which may include the anterior lateral-left balance dysfunction, the anterior lateral-right balance dysfunction, the posterior lateral-left balance dysfunction, and the posterior lateral-right balance dysfunction) is divided into three areas, making up a total of 12 areas, which in turn, make up a total of 12 balance dysfunction types. Each of the 12 areas may be divided into three sub-areas. Thus, a total of 12 balance dysfunction types and a total of 36 sub-areas are defined in FIG. 6, and 36 sub-areas correspond to various locations of the torso of the patient, which also correspond to various locations of the balance compensating vest to be worn by the patient. In FIG. 6, 36 sub-areas are defined, but the present disclosure is not limited thereto, and the number of sub-areas may be less than or more than 36.

Each area and each sub-area of the COG coordinate system illustrated in FIG. 6 corresponds to an area and a sub-areas on the balance compensating vest on which the weight serving as the stimulus is placed. In the example illustrated in FIGS. 6 to 8, an area or a sub area corresponding to each of the anterior balance dysfunction, the posterior balance dysfunction, the lateral-left balance dysfunction, and the anterior lateral-left balance dysfunction is not defined because the balance dysfunction of the patient is unlikely to accurately coincide with the anterior balance dysfunction, the posterior balance dysfunction, the lateral-left balance dysfunction, and the anterior lateral-left balance dysfunction. The anterior balance dysfunction, the posterior balance dysfunction, the lateral-left balance dysfunction, and the anterior lateral-left balance dysfunction can be compensated by the adjacent two areas on the respective sides even though the patient has one of the anterior balance dysfunction, the posterior balance dysfunction, the lateral-left balance dysfunction, and the anterior lateral-left balance dysfunction.

A process for determining an area to which the balance dysfunction of the patient based on the COG value (CGx, CGy) by the processing unit 20B will now be described.

The weight placement position determining unit 50 of the processing unit 20B first determines an area to which the balance dysfunction belongs based on the COG value (CGx, CGy) and determines a position on the balance compensating vest to which the weight is to be attached. For example, one of the 36 areas specified by the COG value (CGx, CGy) is determined as the placement position of the weight. The weight placement position determining unit 50 may determine an area to which the balance dysfunction of the patient belongs among the areas A to L illustrated in FIG. 6, for example, using a correspondence table in which the COG value (CGx, CGy) is associated with one of the areas A to L. The correspondence table is stored in the DB 300 of the storage unit 20C. In FIG. 6, for example, when the direction of the vector V is determined to correspond to the area A, a sub-area to which the vector V belongs among the sub-areas A1 to A3 is determined depending on the length of the vector V or the COG value fluctuation. For example, the weight placement position determining unit 50 may determine the weight placement position to be in A1 or A2 based on a first reference value and the weight placement position determining unit 50 may determine the weight placement position to be in A2 or A3 based on a second reference value.

The values reflected by the first reference value and the second reference value may be of a same type or of different types. For example, the first reference value and the second reference value may both reflect the weight size, or the first reference value may, for example, reflect the weight size and the second reference value may reflect the COG value fluctuation.

A patient having the balance dysfunction corresponding to the sub-area A1 is understood to undergo a more severe balance dysfunction than a patient having the balance dysfunction corresponding to the sub-area A2. The same assessment applies to the other areas (e.g., B to L) and the other sub-areas (e.g., a patient having balance dysfunction corresponding to B1 has more severe balance dysfunction than a patient having balance dysfunction corresponding to B2, and so on).

In the present embodiment, for example, each area (as denoted by the letters A through L) is divided into three sub-areas (as denoted by letters and numbers, e.g., A1, A2 and A3), but this is an example, and each area may be divided into four or more areas. In the present embodiment, the entire area is divided into 12 areas (as denoted by the letters A through L), and each area is subdivided into three sub-areas (as denoted by letters and numbers, e.g., A1, A2, and A3), but this is an example, and the sub-area can be divided into more sub-areas. Therefore, more areas and sub-areas can be used for weight size and placement determination in a balance compensating vest.

The direction of the vector V corresponds to the type of balance dysfunction, and the size of vector V corresponds to the severity of the balance dysfunction. The direction of the vector V corresponds to the position on the balance compensating vest to which the weight is attached, and the length of the vector V corresponds to the weight size of the weight (stimulus).

Figure 7:
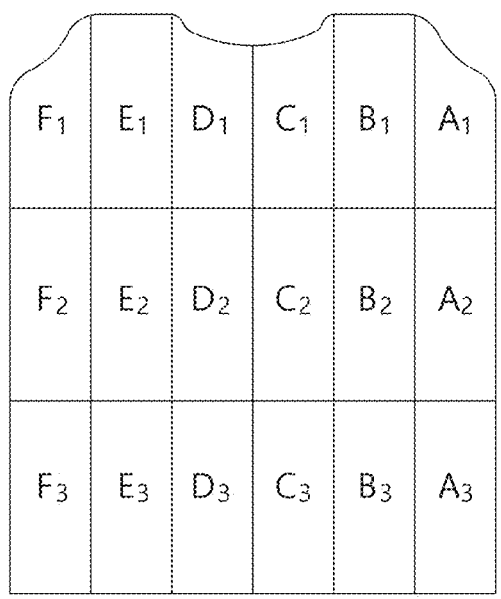
FIG. 7 is a diagram illustrating a backside of a balance compensating vest with indications of weight placement positions according to the present disclosure.
Figure 8:
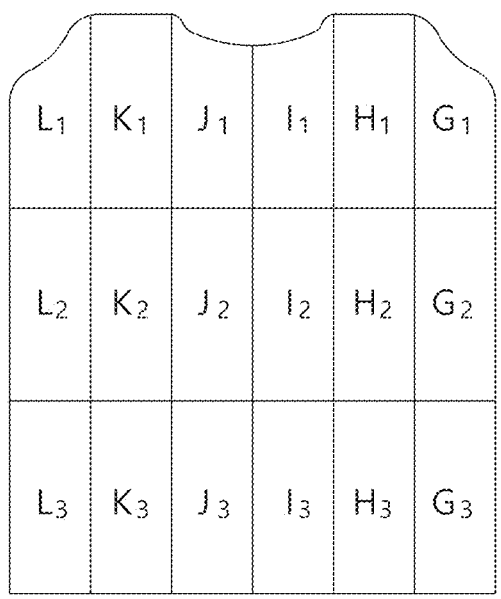
FIG. 8 is a diagram illustrating the front face of a balance compensating vest with indications of weight placement positions according to the present disclosure.

The processing unit 20B determines the balance dysfunction area or direction of the patient and the position to which the weight is to be attached based on the COG value (CGx, CGy) and displays at least one area to which the weight is to be attached using the images illustrated in FIGS. 7 and 8.

As illustrated in FIG. 7, the areas on the −X+Y plane (A1 to A3, B1 to B3, and C1 to C3) and the areas on the +X+Y plane (D1 to D3, E1 to E3, and F1 to F3) are the areas corresponding to the back side of the balance compensating vest, and, as illustrated in FIG. 8, the areas on the +X−Y plane (G1 to G3, H1 to H3, and I1 to I3) and the areas on the −X−Y plane (J1 to J3, K1 to K3, and L1 to L3) are the areas corresponding to the front side of the balance compensating vest.

In determining the weight placement for the patient having the lateral-left balance dysfunction, for example, the weights are to be attached to the areas corresponding to the patient's right shoulder, the right midaxillary line, or the front and back right flank areas of the patient, depending on the location of the vector V. In determining the weight placement for the patient having the lateral-right balance dysfunction, for example, the weights are attached to the left shoulder, the left midaxillary line, or the front and back left flank areas of the patient, depending on the location of the vector V.

Referring to FIG. 6 as an example, the weight is attached to the corresponding sub-areas C3 in the balance compensating vest in FIG. 7 since the vector V is located in the sub-area C3.

In the sub-areas A1, A2, A3, B1, B2, B3, . . . , L1, L2, and L3 illustrated in FIGS. 6, 7, and 8, the same reference numerals correspond to each other. When the vector V is located in the area A1, the weight is attached around the area A1 of the balance compensating vest.

When the vector V is located in a certain (sub) area, one or more weights can be attached in the (sub) area. However, it is not desirable to attach all the weights of the determined sizes to a single (sub) area as concentration of the weight in one part of the patient's body may be burdensome for the patient, the placement of the weight is, preferably, distributed around the end point of the vector V. Referring to FIG. 6 as an example, the end point of the vector V is located in sub-area C3, denoted by a dot, and, in this case, the weights of determined sizes may be placed around the dot as the center, within the sub-area C3. The correspondence relation between the balance dysfunction area of the coordinate system and the area of the balance compensating vest is preferably stored in the storage unit 20C in the form of the correspondence table.

In the example illustrated in FIGS. 7 and 8, A1, B1, C1, D1, E1, F1, G1, H1, I1, J1, K1, and L1 are positioned in the upper parts of the balance compensating vest, and A3, B3, C3, D3, E3, F3, G3, H3, I3, J3, K3, L3 are positioned in the lower parts of the balance compensating vest. The weight attachment effect is greater when the weight is attached to the upper part of the torso of the patient. For example, when the weight of the same size is attached to the position of the sub-area A1, it can cause the COG of the patient to be closer to the origin O, than when the weight of the same size is attached to the position of the sub-area A3.

In general, it is desirable to place the weights in the lower part of the torso because placing the weight in the upper part of the torso would also move the body's COG. However, when the patient's balance dysfunction is represented by sudden leaning or swaying to one direction, the weight placements in patient's upper or middle torso may be considered.

In addition to the balance dysfunction described above, a patient may have a rotational balance dysfunction. The rotational balance dysfunction refers to dysfunction that the patient loses balance when making turns such as U-turn, left turn, or right turn. When the patient has the rotational balance dysfunction, it is desirable to attach the weights on the areas of D and C or J and I (which areas are the areas near the spine of the patient), based on the type of the balance dysfunction and the length of the vector V.

The processing unit 20B may further include a COG value fluctuation calculating unit 70. The COG value fluctuation calculating unit 70 is a body center value fluctuation calculating unit that calculates a body center value fluctuation and calculates a fluctuation of the COG value (CGx, CGy) measured by the COG value calculating unit 60 as an example of the body center value fluctuation.

For patients with a balance dysfunction, their body center value may fluctuate over time, and the COG value fluctuation is an example of such body center value fluctuation and is a value indicating how much the patient having a tremor shakes in the anteroposterior direction and the lateral direction. In the present disclosure, the COG value fluctuation calculating unit 70 may measure the COG value fluctuation by calculating the average fluctuation width of the COG value (e.g., the average fluctuation widths of Wx and Wy in a predetermined time as illustrated in FIG. 14).

Alternatively, the COG value fluctuation in a predetermined time may be calculated using a difference between preceding Wx and Wy values and current Wx and Wy values which are measured at predetermined intervals as illustrated in FIGS. 18 and 19.

FIG. 14 shows the fluctuation of the COG value (CGx, CGy) of the patient A calculated by the COG value fluctuation calculating unit 70. In the example illustrated in FIG. 14, the COG value fluctuation is indicated in units of pounds (weights) but may be indicated in units of COG values or in units of inches (lengths).

In FIG. 14, since the average COG value of the patient A is (−CGx, +CGy), a negative value in the CGx fluctuation (fluctuation lb) indicates that the torso of the patient A moves toward the origin (in the rightward direction in this example), and a positive value indicates that the torso of the patient A moves away from the origin (in the leftward direction in this example). A negative value in the CGy fluctuation (fluctuation lb) indicates that the torso of the patient A moves away from the origin (in the forward direction in this example), and a positive value indicates that the torso of the patient A moves toward the origin (the backward direction in this example).

In FIG. 14, the number of negative values in the CGx fluctuation (fluctuation lb) is 23, whereas the number of positive values is 13, and the number of positive values in the CGy fluctuation (fluctuation lb) is 15, whereas the number of negative values is 21. An average value in the CGx fluctuation (fluctuation lb) in the −X-axis (the left direction) is 0.346 pounds, and an average value in the +X-axis direction (the right direction) is 0.186 pounds, and thus the torso of the patient A shakes in the lateral direction with the width of about 0.532 pounds.

Also, in FIG. 14, an average value in the CGY fluctuation (fluctuation lb) in the −Y-axis direction (the forward direction) is 0.677 pounds, and an average value in the +Y axis direction (the backward direction) is 0.483 pounds, and thus the torso of the patient A shakes in the anteroposterior direction with the width of about 1.16 pounds. It is understood that the CGy fluctuation in the anteroposterior direction is approximately two times larger than the CGx fluctuation in the lateral direction. Also, since the majority of the CGy fluctuations (fluctuation lb) are in the negative, it indicates that the torso of the patient A leans forward more frequently.

With reference to FIG. 14, the majority of the CGx fluctuations (fluctuation lb) are in the negative, which indicates that the torso of the patient A has the strong tendency toward the origin but there is shaking in the lateral direction. Due to the human body structure, the shaking in the lateral direction affects the balance of the patients more than the shaking in the anteroposterior direction affects the balance of the patients. Therefore, when the shaking in the lateral direction is observed together with the shaking in the anteroposterior direction, the patient's ambulatory balance is greatly affected and the patient has a more difficult time finding balance while walking.

In the example of FIG. 14, the patient A has the anterior lateral-left balance dysfunction. More specifically, the patient A is determined to have a balance dysfunction in that the torso of the patient A shakes both in the anteroposterior and lateral directions while frequently leaning leftward.

Accordingly, it is desirable to determine the weight sizes and the weight placement positions in consideration of such analysis.

FIG. 13 is a diagram illustrating a data indicating a weight size obtained by converting a COG value (CGx, CGy) calculated by the COG value calculating unit into a weight for patient A. In the example of FIG. 13, the weight size determined for the patient A is within the range of 2.97 pounds to 3.3 pounds. To simply correct the patient A's COG to the origin, it is desirable to place the weights (selected from the weight size range) on the central back and the midaxillary line of the torso of the patient A. To reduce the tremor, it is desirable to move the weight determined to be placed on the central back to a position between T7 and T9 of the thoracic vertebrae corresponding to a part between the upper part and the lower part of the torso. The tremor may be considered as criterion for determining a sub-area. It is desirable that the weight size to be placed on the patient be as light as possible in order not to cause an additional burden on the patient. Therefore, it is desirable to start with the smallest weight size from the weight size range and gradually increase the weight size until an optimal result for the patient is achieved.

It is desirable to measure the CGx fluctuation and the CGy fluctuation, for example, in units of 0.1 sec or 0.5 sec and display the CGx fluctuation and the CGy fluctuation on the display unit 10B. It is also desirable to display the CGx fluctuation and the CGy fluctuation in real time, for example, using graphs illustrated in FIG. 20 with reference lines indicating normal ranges of the CGx fluctuation and the CGy fluctuation of the normal person. In this case, when the CGx fluctuation and the CGy fluctuation of the patient fall within the normal ranges when the weight is attached to a proper position, a notification may be given using a sound or a display.

The COG value fluctuation can be observed by displaying the trajectory of the change in the COG value (CGx, CGy) displayed on the display unit 10B as illustrated in FIG. 6 through a tracking function. For example, the path (trajectory) in which the COG value (CGx, CGy) changes can be displayed with a specific color.

In this case, before the patient wears the balance compensating vest, the path (trajectory) in which the COG value (CGx, CGy) changes is displayed in a specific color over a relatively large range, but when the patient wears the balance compensating vest to which the weights are attached at proper positions with proper sizes, the COG value (CGx, CGy) of the patient moves closer to the origin with reduced fluctuation, and thus the balance improvement effect of the balance compensating vest can be easily confirmed.

FIGS. 18 and 19 are diagrams illustrating another example of a method of calculating the COG value fluctuation using the Wx value and the Wy value in FIG. 13.

FIG. 18 is a diagram illustrating a method of calculating the fluctuation of the body of the patient, e.g., the CGx value fluctuation. The COG value fluctuation is calculated using a difference (Wx_previous−Wx_current) between a preceding Wx value and a current Wx value which are measured at intervals of one second.

In FIG. 18, when the difference (Wx_previous−Wx_current) between the preceding Wx value and the current Wx value is a negative value, it indicates that the torso of the patient sways rightward, and when the difference (Wx_previous−Wx_current) is a positive value, it indicates that the torso of the patient sways leftward.

When values indicating the difference (Wx_previous−Wx_current) between the preceding Wx value and the current Wx value have the same sign (+ or −), it indicates that the torso of the patient sways in the same direction, and thus the sum of the values having the same sign indicates the CGx value fluctuation.

The sum of the values with the same sign corresponds to the CGx fluctuation in FIG. 18. The CGx fluctuation (%) indicates a percentage (%) of the weight at which the torso of the patient is shaking laterally with respect to the body weight of the patient.

FIG. 19 is a diagram illustrating a method of calculating the CGy value fluctuation (e.g., the degree in which the torso of the patient sways back and forth). The COG value fluctuation is calculated using a difference between an immediately preceding Wy value a current Wy value (Wy_previous−Wy_current) which are measured at intervals of one second.

In FIG. 19, when the difference (Wy_previous−Wy_current) between the preceding Wy value and the current Wy value is a negative value, it indicates that the torso of the patient sways forwards, and when the difference (Wy_previous−Wy_current) is a positive value, it indicates that the torso of the patient sways backward.

When values indicating the difference (Wy_previous−Wy_current) between the preceding Wy value and the current Wy value have the same sign (+ or −), it indicates that the torso of the patient sways in the same direction, and thus the sum of the values having the same sign indicates the CGy value fluctuation.

The sum of the values with the same sign corresponds to the CGy fluctuation in FIG. 19. The CGy fluctuation (%) indicates a percentage (%) of the weight at which the torso of the patient is shaking forward or backward with respect to the body weight of the patient.

As illustrated in FIGS. 18 and 19, when the tremor of the patient is measured using the difference (Wx_previous−Wx_current) between the preceding Wx value and the current Wx value and the difference (Wy_previous−Wy_current) between the preceding Wy value and the current Wy value, it is possible to measure the COG value fluctuation (tremor) of the patient regardless of the patient's position on the platform 10C because the measurement is performed using only the preceding value and the current value. The tremor of the patient can be accurately measured even when the patient is not standing exactly in a certain position. Therefore, it is possible to measure and correct the patient's balance dysfunction first, and then, measure and correct the patient's tremor. For example, a patient with both balance dysfunction and tremor may be wearing the balance compensating vest (as a result of measuring and correcting balance dysfunction) when the same patient is being measured and corrected for the tremor, as the tremor of the patient can be measured accurately regardless of the standing position of the patient.

If the tremor is out of the normal range, the tremor can be reduced by moving the weight already placed on the patient for correcting balance dysfunction up or down within the same area (for example, within the area C in FIG. 6 for the patient A) without changing the basic weight placement position provided for correcting the balance dysfunction. For example, the weight placed on the sub-area C3 is moved up to the sub-area C2 or C1 to reduce the tremor.

When the values corresponding to the CGx fluctuation (%) and the CGy fluctuation (%) in FIG. 18 and FIG. 19 are less than a predetermined value (for example, 0.5%), the CGx fluctuation and the CGy fluctuation (e.g., the tremor) of the patient may be regarded as being within the normal range.

Figure 20:
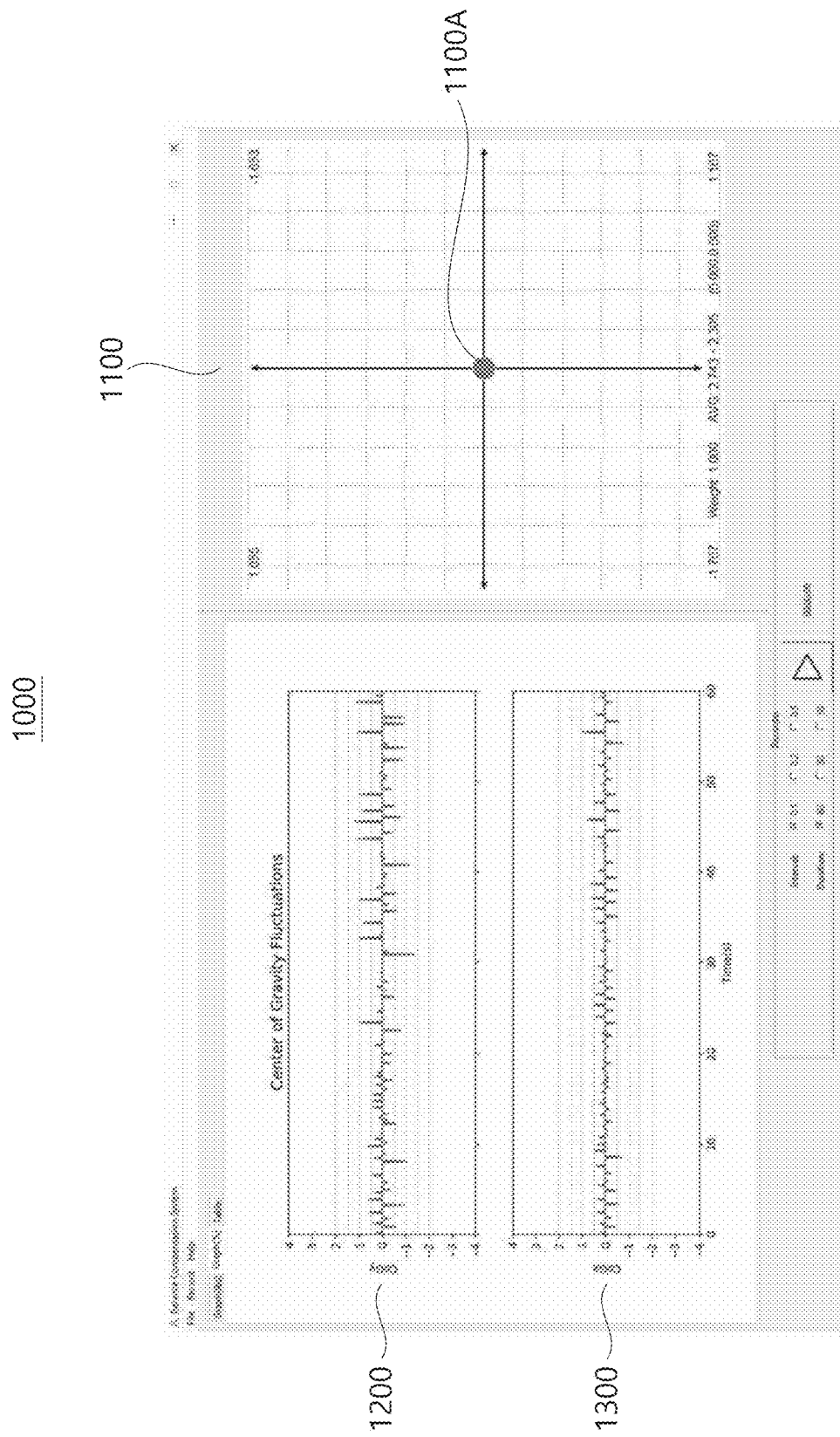
FIG. 20 is a diagram illustrating an operation screen 1000 of a balance compensation program, and is a diagram illustrating measurement results in a state in which a patient is not wearing a balance compensating vest according to the present disclosure.

FIG. 20 is a diagram illustrating an operation screen 1000 of the balance (tremor) compensation program. The operation screen 1000 includes a COG coordinate system 1100, a COGy value fluctuation graph 1200, and a COGx value fluctuation graph 1300. The COG coordinate system 1100 includes a circular cursor 1100A, and the position of the cursor 1100A indicates the COG position of the patient on the COG coordinate system.

FIG. 20 illustrates a screen showing a balance compensation measurement result. The measurement values LC1, LC2, LC3, and LC4 of the respective sensors are displayed on four corners of the COG coordinate system 1100, and the cursor 1100A is located at the origin because the patient's balance dysfunction is not being measured, as the patient is not standing on the body center measuring apparatus. In FIG. 20, −1.767, 1.167, −1.653, and 1.055 are displayed as LC1, LC2, LC3, and LC3, respectively. Before measuring the patient's COG, LC1, LC2, LC3, and LC3 should be calibrated to 0, and this is done by leveling the platform 10C. When the platform 10C is perfectly leveled, LC1, LC2, LC3, and LC3 should be at zero (0.000), assuming that that there is no sensitivity error inherent in each load cell. AVG 2.743~2.305 displayed at the bottom of the COG coordinate system 1100 indicates the measured weight size range of the patient.

The COGy value fluctuation graph 1200 and the COGx value fluctuation graph 1300 show the results of performing the measurement in units of 0.1 seconds for 60 seconds in a state in which the patient was not wearing the balance compensating vest. The COGy value fluctuation graph 1200 and the COGx value fluctuation graph 1300 are graphs displaying the CGx fluctuation (%) and the CGy fluctuation (%) calculated in a manner similar to the manner described for FIGS. 18 and 19.

The operation screen includes a portion for setting a measurement interval of a recorder for recording the COGy value fluctuation graph 1200 and the COGx value fluctuation graph 1300 and a portion for setting a measurement duration, and a record start button.

In the COGy value fluctuation graph 1200, a negative value indicates the patient's body shaking in the forward (anterior) direction, a positive value indicates the patient's body shaking in the backward (posterior) direction, a negative value in the COGx value fluctuation graph 1300 indicates the patient's body shaking in the rightward direction, and a positive value in the COGx value fluctuation graph 1300 indicates the patient's body shaking in the leftward direction.

The operator can compare anterior shaking with posterior shaking of the patient while viewing the peak values in the graph and compare rightward shaking with leftward shaking while viewing the peak values in the graph. Thus, the operator is able to adjust the weight placement position with reference to the peak values.

After the balance compensation program is executed, the cursor 1100A of the COG coordinate system 1100 displays the COG value (CGx, CGy) of the patient in real time while the patient is standing on the body center measuring apparatus 100. When the operator sets the measurement duration and the measurement interval and then pushes the record start button, a screen as illustrated in FIG. 20 is displayed after the measurement duration.

Some patients may have balance dysfunction without tremors whereas some patients may have balance dysfunction with tremors of varying degrees. With respect to the balance dysfunction patients with tremors, the operator may take additional steps to adjust the weight placements as described below to reduce the tremor of the patient.

For measuring the COG value fluctuation for tremor of a patient, the techniques described with the reference to FIGS. 18 and 19 are used. For tremor measurements (e.g., COG value fluctuations for tremor), the patient may stand on positions other than the FL and FR position illustrated in FIG. 2 since the COG of the patient can be moved to the origin O by the weight sizes and the placements determined by the above-described steps, and the steps for reducing the tremor can be performed, for example, by moving the weights within the same area as described above. According to the technique described with reference to FIGS. 18 and 19, the patient stands on the platform 10C of the body center measuring apparatus 100 with a comfortable posture since the previous value is compared with the present value.

The lateral shaking and the anteroposterior shaking of the patient are displayed through the graphs in addition to the COG of the patient value, the operator or the patient can easily understand the lateral shaking and the anteroposterior shaking of the patient and take additional steps for reducing the tremor of the patient. The operator performs an adjustment for reducing the tremor within the determined basic weight placement positions while viewing the lateral shaking and the anteroposterior shaking of the patient.

Figure 21:
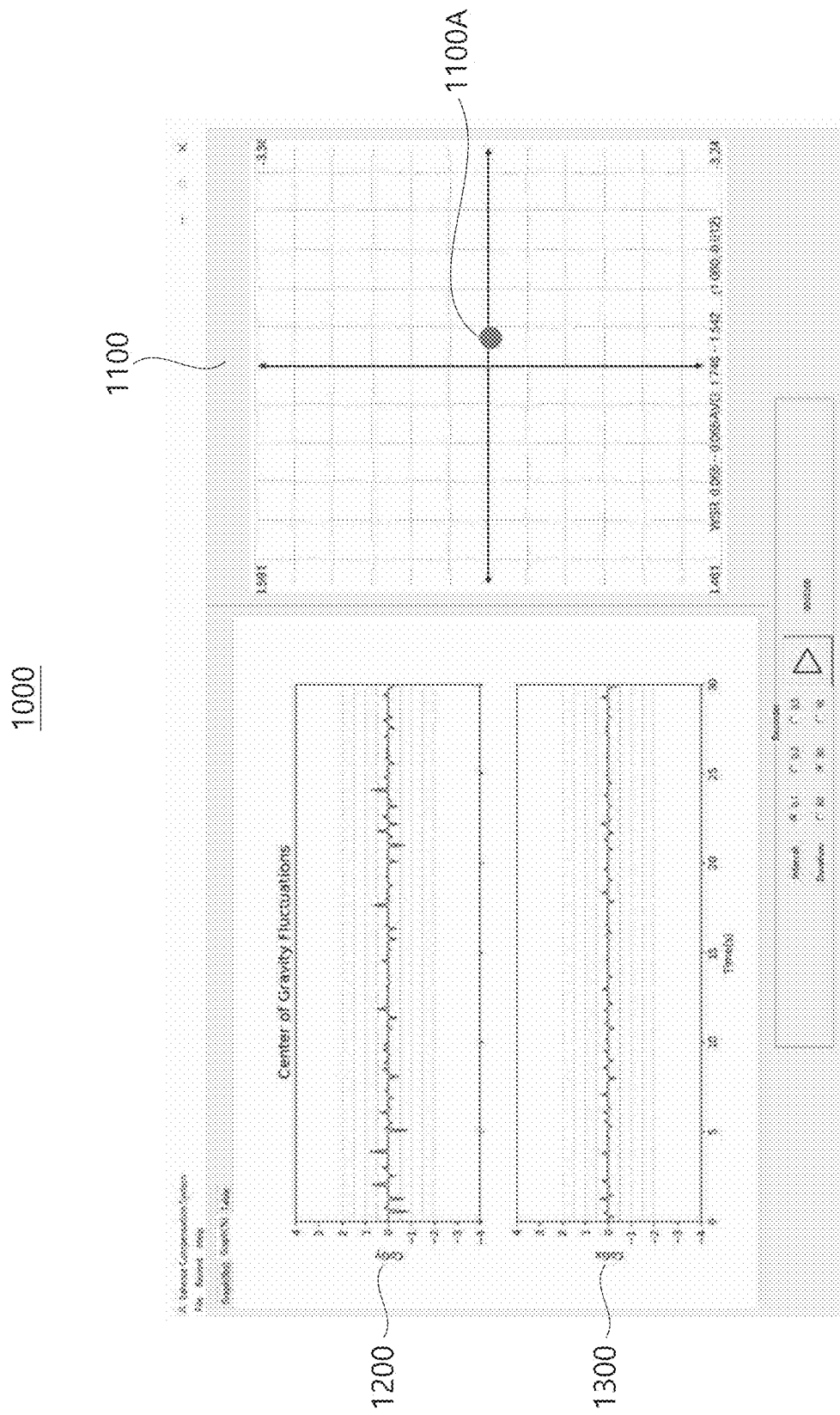
FIG. 21 is a diagram illustrating an operation screen 1000 of a balance compensation program, and is a diagram illustrating measurement results in a state in which a patient is wearing a balance compensating vest according to the present disclosure.

FIG. 21 is a graph illustrating a result of measuring the COG value fluctuation of the patient wearing the balance compensating vest. As illustrated in FIG. 21, when the weight size determined by the weight size determining unit 40 is attached to the placement position determined by the weight placement position determining unit 50, the COG of the patient is close to the origin, and the COG value fluctuation of the patient also falls within the normal range. Thus, the tremor of the patient is reduced when the COG value fluctuation of the patient falls within the normal range.

The reduction of tremor in the patients with balance disorders has many benefits. For example, headaches, double vision, and the like are the symptoms often accompanied with balance order patients with tremors, and the reduction of tremor, often result in improvements of these symptoms, resulting in the improvement of the patient's quality of life.

In FIGS. 20 and 21, 0.5% (a range of +0.5% and −0.5%) of the body weight of the patient is set as the normal range in which the gait of the patient can be improved, and the tremor of the body of the patient can be improved. The normal range is indicated by a dotted line. Thus, the operator, by viewing whether or not the COG value fluctuation is within the normal range, may easily detect whether or not the patient has a tremor and whether or not the tremor of the patient is reduced by the application of the balance (tremor) compensating vest on the patient.

The COGy value fluctuation graph 1200 and the COGx value fluctuation graph 1300 illustrated in FIG. 20 may be displayed in real time. After the balance (tremor) compensation program is executed, the COGy value fluctuation graph 1200 and the COGx value fluctuation graph 1300 may be displayed in real time while the patient is standing on the platform 10C of the body center (tremor) measuring apparatus 100.

In this case, the weights of determined weight size are attached to the patient standing on the body center measuring apparatus 100 with reference to the determined weight size, the COGy value fluctuation graph 1200 and the COGx value fluctuation graph 1300 are displayed in real time while showing the peak values indicating the lateral shaking and the anteroposterior shaking. Thus, in addition to whether or not the COG of the patient is improved, the operator can easily understand whether or not the tremor of the patient is reduced through the COGy value fluctuation graph 1200 and the COGx value fluctuation graph 1300, whereby both the COG of the patient and the tremor of the body of the patient can be easily compensated for in a short time.

For example, when the COGy value fluctuation graph 1200 shows a peak indicating the anterior shaking, the operator can move the weight placed on the back side of the balance compensating vest up or move the weight placed on the front side of the balance compensating vest down, whereas when the COGy value fluctuation graph 1200 shows a peak indicating the posterior shaking, the operator can move the weight placed on the back side of the balance compensating vest down or move the weight placed on the front side of the balance compensating vest up.

The weight to attach on the patient, preferably, has a hook and loop fastener or the like, allowing easy attachment and detachment, and it is possible to find a correct placement position for reducing the tremor of the patient by attaching and detaching the weight on the balance (tremor) compensating vest while the patient is standing on the platform 10C of the body center (tremor) measuring apparatus 100.

FIG. 22 is a diagram illustrating values to be recorded in a table after the recorder in FIG. 21 is executed. Once the recorder in FIG. 21 is executed, the COGy value fluctuation graph 1200 and the COGx value fluctuation graph 1300 illustrated in FIG. 21 are displayed, and at the same time, the body weight of the patient, the average COG value (CGx, CGy), and the weight size range are stored in the table illustrated in FIG. 22. Further, once the recorder is executed, for example, the largest three values, of the positive value CGy fluctuation, of the negative value CGy fluctuation, of the positive value CGx fluctuation, and of the negative value CGx fluctuation are stored.

If the operator determines that the COG and the tremor of the patient are not sufficiently corrected with reference to the COGy value fluctuation graph 1200 and the COGx value fluctuation graph 1300 with the weight size calculated by the weight size determining unit 40 attached to the placement position determined by the weight placement position determining unit 50, the operator may adjust the weight size and the placement position with reference to the values recorded in the table of FIG. 22.

On the other hand, the operator may adjust the weight size and the placement position while viewing the operation screen of the balance compensation program illustrated in FIG. 21 with reference to the weight size calculated in the weight size determining unit 40 and the placement position determined by the weight placement position determining unit 50.

It is possible to adjust the weight size and the placement position so that the COG of the patient moves toward the origin while viewing the COG coordinate system 1100, and it is also possible to adjust the weight size and the placement position so that the tremor falls within the normal range while looking at the COGy value fluctuation graph 1200 and the COGx value fluctuation graph 1300.

The patient may feel discomfort when the weight (as determined by the weight size determining unit 40) is applied to the patient. It is likely that the heavier weight will put more strain on the patient. Therefore, it is desirable to adjust the weight, within the weight size range, provided by the weight size determining unit 40 to the least burdensome weight size possible, so long as the COG of the patient is stable within the base of support, and the patient's tremor fall within the normal range.

Assuming that the COG of the patient is stable within the base of support, it is desirable to adjust the weights to affect the patient's lateral balance so that CGx value is as close to the origin as possible, rather than adjusting anteroposterior balance (e.g., CGy value) to reduce the weight size placed on the patient.

It is possible for the weight placement position determining unit 50 to present two, three or more combinations of the weight placement positions from which the patient can select.

It is desirable to select a combination of the weight placement positions, after performing other tests such as gait tests, lunging tests, rotation tests, tandem stance tests, and repeated sitting in and standing from chair tests.

As illustrated in FIG. 15, the processing unit 20B may store the COG value (CGx, CGy) of the patient, the balance dysfunction type, the weight size, the COG value fluctuation, and the weight placement position in the database 300 as the balance compensation history information. FIG. 15 illustrates the balance compensation history information stored in the database 300.

In a case in which the balance compensation history information of a plurality of patients is stored in the DB 300, when the processing unit 20B performs learning such as machine learning, it is possible to determine weight placement position on the basis of the type of balance dysfunction, the weight size, and the COG value fluctuation. As more data are accumulated and analyzed, it is possible to enhance the weight size determinations and placements for various balance disorder patients.

Although the body center measuring apparatus 100 and the information processing apparatus 200 are described as separate devices in the present embodiment, the functions of the body center measuring apparatus 100 and the functions of the information processing apparatus 200 may be implemented in a single device. For example, the processing unit 20B and the storage unit 20C of the information processing apparatus may be implemented in the body center measuring apparatus 100.

Figure 17:
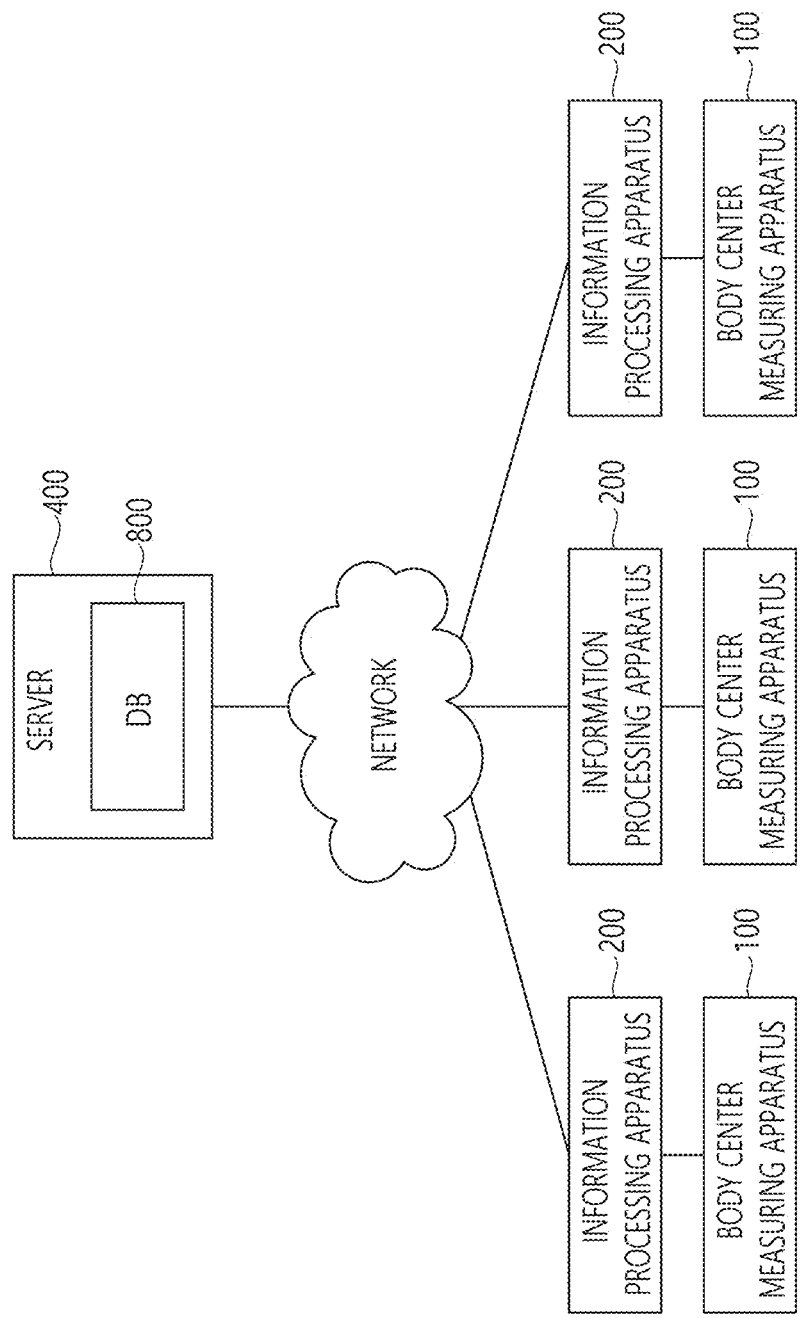
FIG. 17 is a diagram illustrating a balance compensation system according to the present disclosure.

Although the DB 300 storing the balance compensation history information and the balance compensation program is described as installed in the information processing apparatus 200 in the present embodiment, the DB 300 may be installed and stored in a server device 400 which is connected to the information processing apparatus 200 in a wired or wireless manner as illustrated in FIG. 17. In this case, a plurality of information processing apparatuses 200 can be connected via a network, and thus the weight size and the weight placement position can be determined by learning performed using the balance compensation history information of more patients.

When a plurality of information processing apparatuses 200 are connected to the server device 400, and the balance compensation history information obtained by the information processing apparatuses 200 is stored in the DB 300 of the server device, for example, the machine learning is performed, so that the more advanced balance compensation program can be provided, and the information processing apparatus 200 can determine the weight size and the weight placement position using the balance compensation program, thereby realizing excellent balance compensation performance.

Meanwhile, it is desirable for the patient to wear the balance compensating vest with the size coinciding with the body shape of the patient. Particularly, it is desirable to adjust the lower end of the balance compensating vest to correspond to the COG of the patient. In the case of women, the COG is at a position of 55% of the height, and in the case of men, the COG is at a position of 57% of the height. The COG of normal humans is generally located just below the belly button. Preferably, the position of the bottom of the balance compensating vest coincides with the position of the COG of the patient.

Preferably, the balance compensating vest is made of a lightweight material which can retain its shape. For example, the hook of the hook and loop fastener is attached to the weight (stimulus), and the loop of the hook and loop fastener is attached to the inside of the balance compensating vest, so that the weight (stimulus) is repeatedly attachable and detachable from the balance compensating vest, and when the balance of the patient is determined to be sufficiently compensated, the weight size and the weight placement position are determined.

Alternatively, when the weight size and the weight placement position are determined, the weights may be fixedly attached to the balance compensating vest or clothing worn by the patient by sewing or the like. Balance compensation vests of various sizes may be prepared in advance, and when the patient visits and chooses the balance compensation vest with the size suitable for the body shape of the patient, the weight size and the weight placement position are determined by the balance compensation system 1000, and the weights are fixedly attached to the chosen balance compensation vest in accordance with the weight size and the weight placement position determined by the balance compensation system 1000.

The balance compensating vest is an example, and the balance compensating device may have various forms. For example, the balance compensating device may be women's sports bra or a suspender to which the weight can be attached. For example, the balance compensating device may be an orthotic, a brace, or any object with the weight size and the weight placement position determined by the balance compensation system 1000. The object with the weight size and the weight placement position determined by the balance compensation system 1000 may be made by a 3D printer or the like. The weight (stimulus) can be integrated into the balance compensating device.

A material of the weight is not particularly limited, and rubber, silicone, gel, sand, liquid or the like may be used. For example, Flexible Metal® available from Ironwear® may be used as the weight (stimulus). For fine balance compensation, preferably, the weight can be sized in units of one pound (lb), 0.5 pounds (lb), 0.25 pounds (lb), 0.125 pounds (lb), and the like. One weight or several weights may be used to satisfy the determined weight size at the determined weight placement position.

Next, an operation of the balance compensation system 1000 of the present embodiment will be described using a flowchart.

Figure 9:
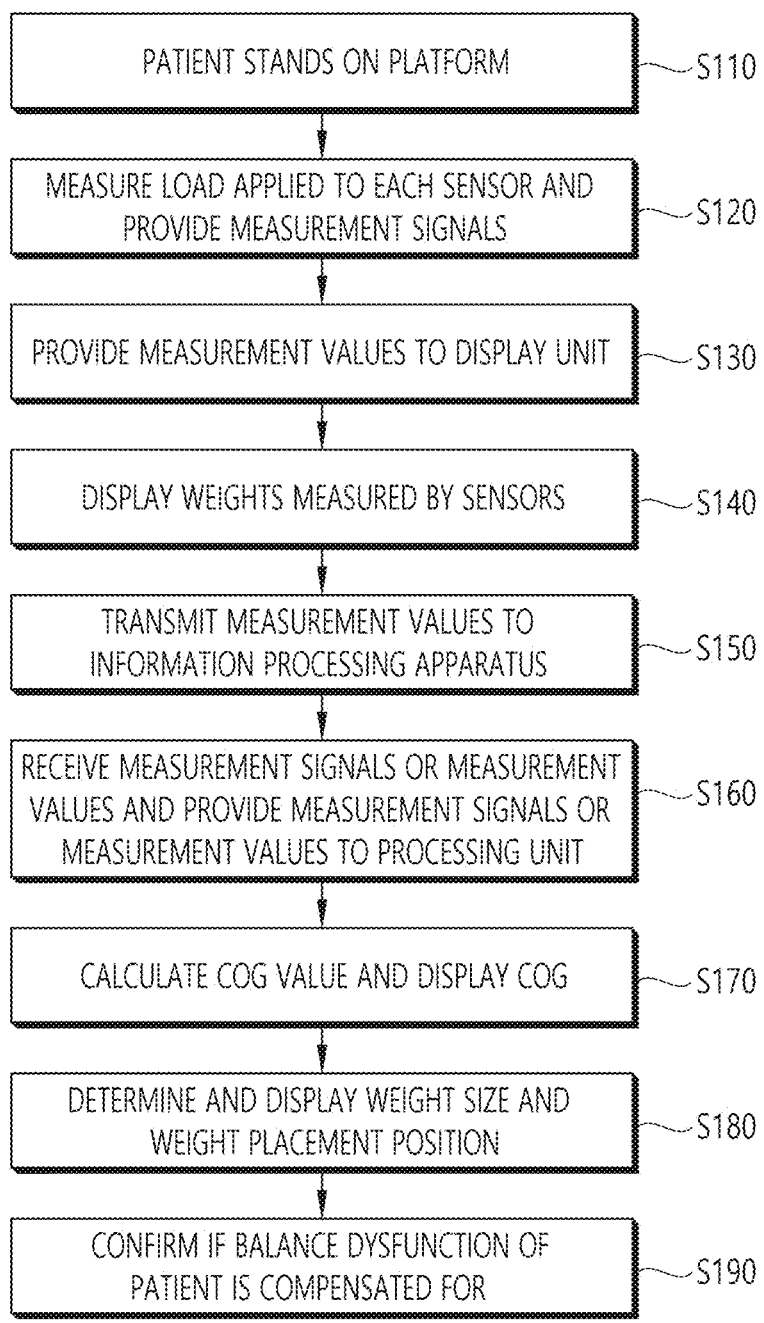
FIG. 9 is a flowchart illustrating an operation of a balance compensation system according to the present disclosure.

FIG. 9 is a flowchart illustrating an operation of the balance compensation system 1000.

The operation of the balance compensation system 1000 of the present embodiment starts when the patient stands on the platform 100C of the body center measuring apparatus 100.

In step S110, it is determined whether or not the patient stands on the platform 100C of the body center measuring apparatus 100. If it is determined in step S110 that the patient stands on the platform 100C of the body center measuring apparatus 100, in step S120, the sensors 10LC1, 10LC2, 10LC3, and 10LC4 measure the applied loads and provide the measurement signals to the processing unit 10C.

In step S130, the processing unit 10C performs a process such as signal amplification or digital conversion on the measurement signals, obtains the measurement values LC1, LC2, LC3, and LC4, and transmits the measurement values LC1, LC2, LC3, and LC4 to the display unit 10B.

In step S140, the display unit 10B receives the measurement values, and displays the weights measured by the sensor unit.

If the body center measuring apparatus 100 is connected to the information processing apparatus 200 in a wired or wireless manner, in step S150, the body center measuring apparatus 100 transmits the measurement signals or the measurement values to the information processing apparatus 200.

If the body center measuring apparatus 100 is not connected to the information processing apparatus 200, the process of steps 150 to S180 may be skipped and the operator may perform the process of determining the weight size and the weight placement position (step S180) and the process of confirming whether or not the balance of the patient is compensated for (step S190) manually with reference to the measurement values displayed on the display unit 10B.

In step S160, the input unit 20A receives the measurement signals or measurement values and provides the measurement signals or the measurement values to the processing unit 20B.

In step S170, the processing unit 20B calculates the COG value (CGx, CGy) of the patient based on the measurement values LC1, LC2, LC3, and LC4 and causes the COG value (CGx, CGy) of the patient to be displayed on the display unit 20D as illustrated in FIG. 6.

In step S180, the processing unit 20B determines the type of balance dysfunction of the patient, the weight size for compensating for the balance dysfunction, and the weight placement position on the balance compensating vest at which the weights corresponding to the weight size are attached on the basis of the COG value (CGx, CGy), and causes the weight size and the weight placement position to be displayed on the display unit 20D.

In step S190, when the patient wears the balance compensating vest with the weight size and the weight placement position determined in step S180 and stands on the platform 10C of the body center measuring apparatus 100 or the weight size and the weight placement position determined in step S180 are applied to the balance compensating vest worn by the patient standing on the platform 10C of the body center measuring apparatus 100, it is possible to confirm whether the balance of the patient is compensated.

The determination of whether the balance of the patient is compensated in step S190 by the weight size and the weight placement position determined in step S180 can be performed based on the measurement values LC1, LC2, LC3, and LC4 displayed on the display unit 10B or through the operation screen of the balance compensation program illustrated in FIGS. 20 to 22 displayed on the display unit 20D.

When the measurement values LC1, LC2, LC3, and LC4 displayed on the display unit 10B are substantially equal to one another, the COG of the patient can be regarded as being corrected, and when the COG of the patient is corrected, the COG of the patient is located at the origin O illustrated in FIG. 6. In addition, in the operation screen of the balance compensation program illustrated in FIGS. 20 to 22, the COG value fluctuation falls within the normal range as well.

Therefore, operators with no training in physical therapy or medicine can use the devices, system, apparatus, and methods disclosed in the present disclosure to make the balance compensating vest capable of compensating for the balance dysfunction of the patient.

In addition, the patient is also able to understand that the patient's balance dysfunction is corrected by the balance compensating vest by viewing that the COG of the patient is moved to the normal position.

Figure 10:
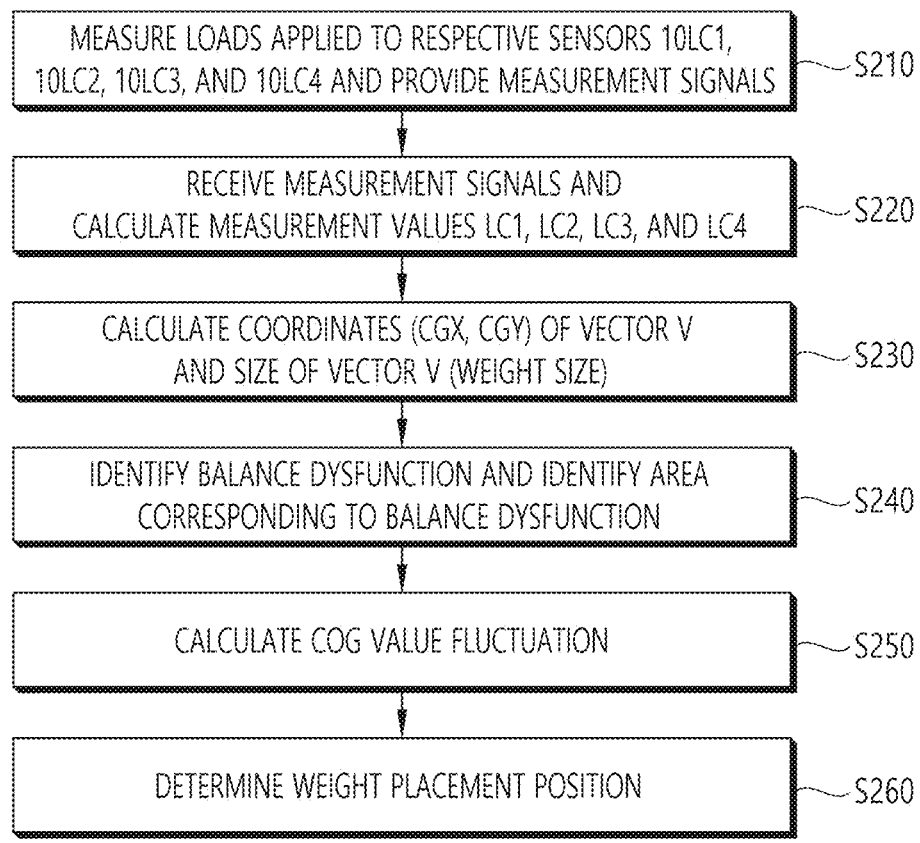
FIG. 10 is a flowchart illustrating a process of making a balance compensating vest by determining a size and a placement position of a weight attached to the balance compensating vest according to the present disclosure.

FIG. 10 is a flowchart illustrating a process of determining the weight size and the weight placement position of the balance compensating vest and making the balance compensating vest.

In step S210, when the patient stands on the platform 10C of the body center measuring apparatus 100, the sensors 10LC1, 10LC2, 10LC3, and 10LC4 output the measurement signals indicating the loads applied to the respective sensors.

In step S220, the measurement signals are received and the measurement values LC1, LC2, LC3, and LC4 are calculated.

In step S230, the coordinates (CGx, CGy) of the vector V and the length of the vector V are calculated based on the measurement values LC1, LC2, LC3, and LC4.

In step S240, the type of balance dysfunction is identified based on the coordinates (CGx, CGy) of the vector V and the size (W1) of the vector V, and the area corresponding to the balance dysfunction is identified.

In step S250, the COG value fluctuation is calculated.

In step S260, an area on the balance compensating vest corresponding to the identified area corresponding to the balance dysfunction is identified, and the weight placement position is determined based on the identified area and the COG value fluctuation.

In step S260, at least one combination of one or more areas can be presented as the area corresponding to the identified balance dysfunction, and when a plurality of combinations of areas are presented, a preferred combination can be determined through conducting more tests such as gait test, lunge test, rotation test, and sitting in chair test.

Figure 11:
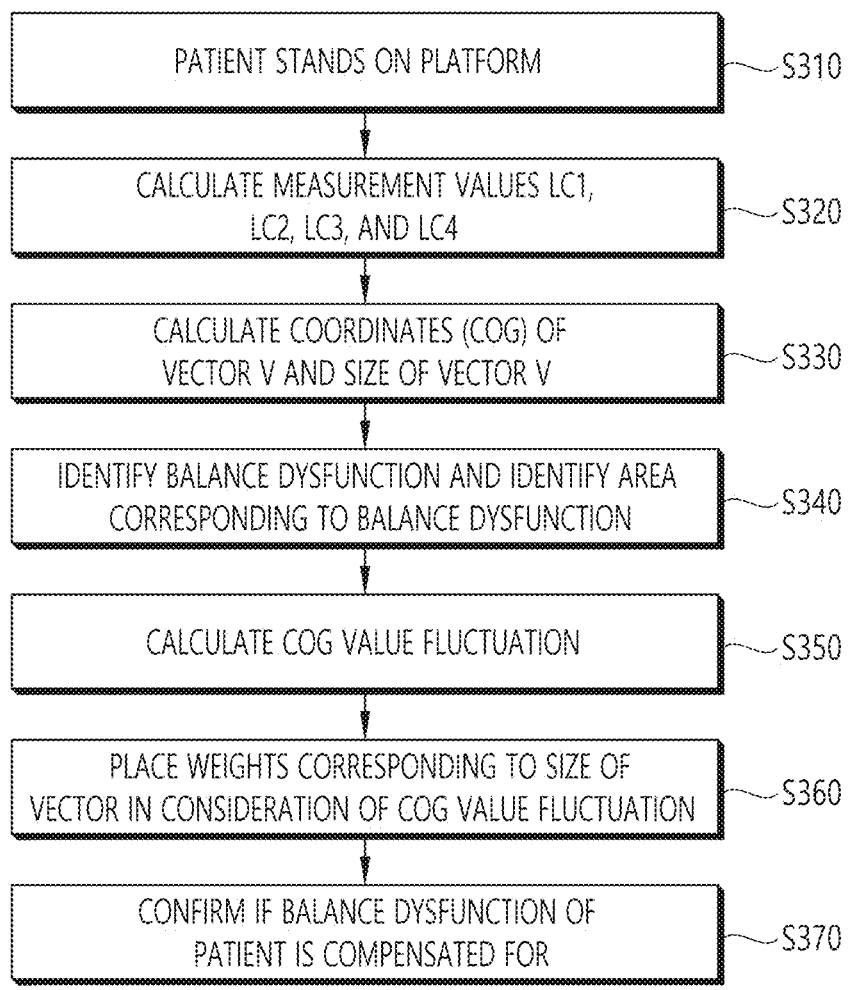
FIG. 11 is a flowchart illustrating a method of compensating balance of a patient by an operator when an information processing apparatus is not connected to a body center measuring apparatus according to the present disclosure.

FIG. 11 is a flowchart illustrating a method of compensating for the balance of the patient when the information processing apparatus 200 is not connected to the body center measuring apparatus 100.

In step S310, the patient stands on the platform 10C of the body center measuring apparatus 100, and the sensors 10LC1, 10LC2, 10LC3, and 10LC4 output the measurement signals indicating the loads applied to the respective sensors.

In step S320, the measurement values LC1, LC2, LC3, and LC4 are calculated from the measurement signals.

In step S320, the display unit 10B displays the measurement values LC1, LC2, LC3, and LC4.

The XY coordinate system indicating the COG value (CGx, CGy) illustrated in FIG. 6 may be displayed.

In step S330, the operator calculates the coordinates (CGx, CGy) of the vector V and the length of the vector V using Formula (1) and $\sqrt{(Wx^2+Wy^2)}$ with reference to the measurement values LC1, LC2, LC3, and LC4 displayed on the display unit 10B.

In step S340, the operator identifies the type of balance dysfunction based on the coordinates of the vector V and the length of the vector V and identifies an area corresponding to the balance dysfunction.

In step S350, the COG value fluctuation is calculated.

In step S360, in a state in which the patient stands on the platform 10C of the body center measuring apparatus 100, the operator places the weights corresponding to the length of the vector on the areas of the balance compensating vest corresponding to the balance dysfunction area in view of the COG value fluctuation.

If the patient does not correctly stand on the positions (FL, FR) indicated on the platform 10C of the body center measuring apparatus 100, the weight size and the weight placement position described above may deviate from the ideal weight size and weight placement position may include errors.

To reduce the occurrence of measurement errors, the process of step S310 to step S320 is, preferably, repeatedly performed, and one of the measurement values LC1, LC2, LC3, and LC4 which are measured repeatedly may be employed, or an average of the measurement values LC1, LC2, LC3, and LC4 which are measured repeatedly may be employed.

In addition, although the weights are attached to the balance compensating vest in accordance with the weight size and the weight placement position described above, the COG of the patient may not perfectly coincide with the origin "O" when the patient does not correctly stand on the position (FL, FR) displayed on the platform 10C of the body center measuring apparatus 100. In this case, the operator may finely adjust the weight size and the weight placement position which are determined above.

However, since it may not be easy for the patient to accurately stand on the positions FL and FR indicated on the platform 10C of the body center measuring apparatus 100, a sensor plate 10C' capable of detecting the COG coordinates of both feet of the patient using a touch detection technique or a pressure detection technique may be employed as the platform 10C as illustrated in FIG. 17. In another embodiment, a touch detection technique or a pressure detection technique may be used, for example, if the patient is unable to stand on the positions FL and FR indicated on the platform 10C of the body center measuring apparatus 100.

Figure 16:
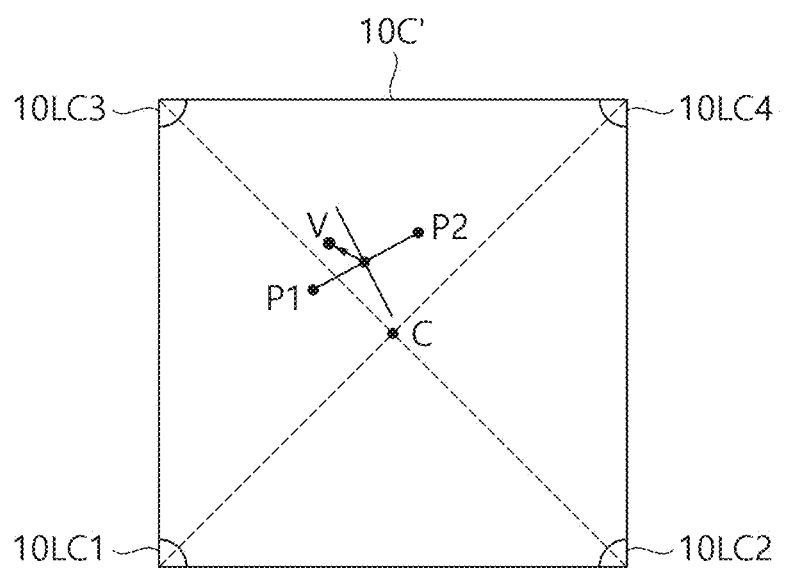
FIG. 16 is a diagram illustrating a platform of a body center measuring apparatus which is constituted by a sensor plate that senses a touch or pressure according to the present disclosure.

Referring to FIG. 16, a coordinate system (a second coordinate system) is defined such that a straight line connecting the COG coordinates (positions P1 and P2) of both feet of the patient detected by the sensor plate 10C' is set as an X' axis, a middle point between the positions P1 and P2 of the feet of the patient is set as the origin, and a straight line passing perpendicularly through the origin is set as a Y' axis.

Then, the COG value (CGx, CGy) (first COG value) is calculated through the COG coordinate system (first coordinate system) illustrated in FIG. 6. A new COG value (CGx', CGy') (second COG value) is obtained by calculating the distances of the COG value (CGx, CGy) (first COG value) from the X' axis and the Y' axis in the second coordinate system.

The identification of the balance dysfunction type, the COG value fluctuation calculation, the weight size calculation, and the weight placement position determination are performed using the second COG value (CGx', CGy') using a method similar to the method described above.

Since the platform 10C is constituted by the sensor plate 10C', the patient need not stand on the positions FL and FR accurately for accurate COG measurement. The COG value (CGx, CGy) of the patient can be accurately measured regardless of the standing positions of the patient.

In another example, a straight line connecting the COG coordinates (positions P1 and P2) of the feet of the patient detected by the sensor plate 10C' is set as an X' axis, and the coordinates (Cx, Cy) of the middle point between the positions P1 and P2 of the feet of the patient, and the COG value (CGx, CGy) of the patient is obtained.

Then, (CGx−Cx, CGy−Cy) is obtained. This is to convert the COG value (CGx, CGy) into coordinates corresponding to the original origin (C), but in this state, a straight line connecting P1 and P2 is not parallel to the X-axis.

Thereafter, an angle θ between the straight line connecting P1 and P2 and the X-axis is calculated, and rotation conversion corresponding to the angle θ is performed on (CGx–Cx, CGy–Cy), whereby the body center or COG value (CGx', CGy') of the patient with respect to the origin O can be calculated.

The rotation conversion corresponding to the angle θ for (CGx–Cx, CGy–Cy) can be performed by Formulas (3) and (4). Formula (3) corresponds to a formula for clockwise rotation conversion, and Formula (4) corresponding to a formula for counterclockwise rotation conversion.

$$CGx'=x \cos θ+y \sin θ, CGy'=y \cos θ-x \sin θ \qquad (3)$$

$$CGx'=x \cos θ-y \sin θ, CGy'=y \cos θ+x \sin θ \qquad (4)$$

(here, x=CGx–Cx, y=CGy–Cy)

In step S370, when the COG of the patient is determined to coincide with the origin "O" through the display unit 10B or 20D, the weights are attached to the balance compensating vest to be worn by the patient in accordance with the weight size and the weight placement position determined.

In step S370, when the COG of the patient does not coincide with the origin O, the operator may manually adjust the weight size and the weight placement position as described above.

The example in which the weight size and the weight placement position are determined using the average value of the COG values of the patient measured for a predetermined period has been described above. This technique is effective for patients having mild tremor.

In the case of the patients having a severe tremor, it is desirable to determine the weight size and weight placement position using two or more COG values affecting the balance of the patient. In the case of patients having a severe tremor, the torso sways in two or more directions, and thus it is desirable to identify the balance dysfunction in various directions and determine the weight size and the placement position in each of the directions in which the balance dysfunction is identified.

FIGS. 23 to 27 are diagrams illustrating another example of the balance compensation process of determining the weight size and the weight placement positions according to the present disclosure.

Figure 23:
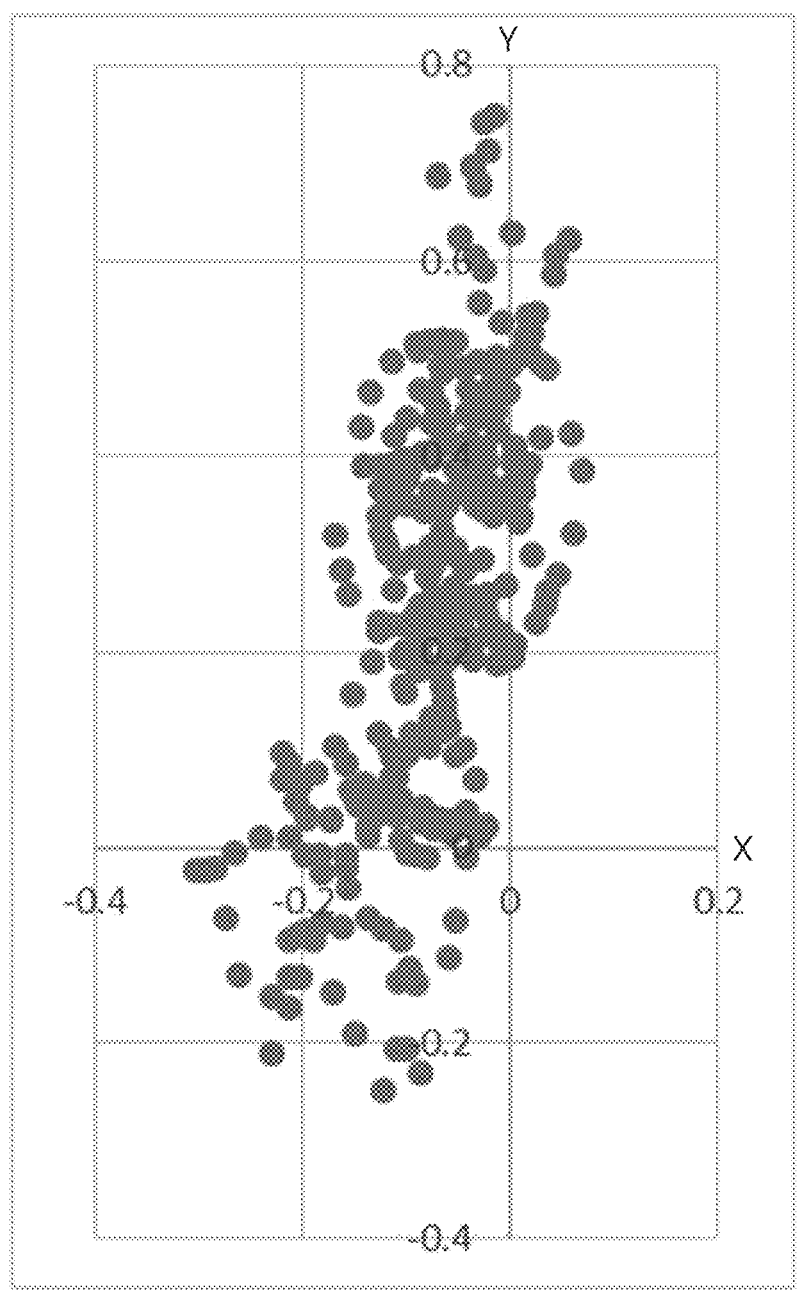
FIG. 23 is a distribution diagram illustrating COG values of a patient which are measured in units of 0.1 seconds for 30 seconds according to the present disclosure.

FIG. 23 is a distribution diagram illustrating the distribution of COG values of the patient measured for 30 seconds in units of 0.1 seconds. As illustrated in FIG. 23, the COG values of the patient are concentrated on the +X+Y plane, the –X+Y plane, and the –X–Y plane. This means that the torso of the patient shakes in the right anterior direction, the left anterior direction, and the left posterior direction.

Figure 24:
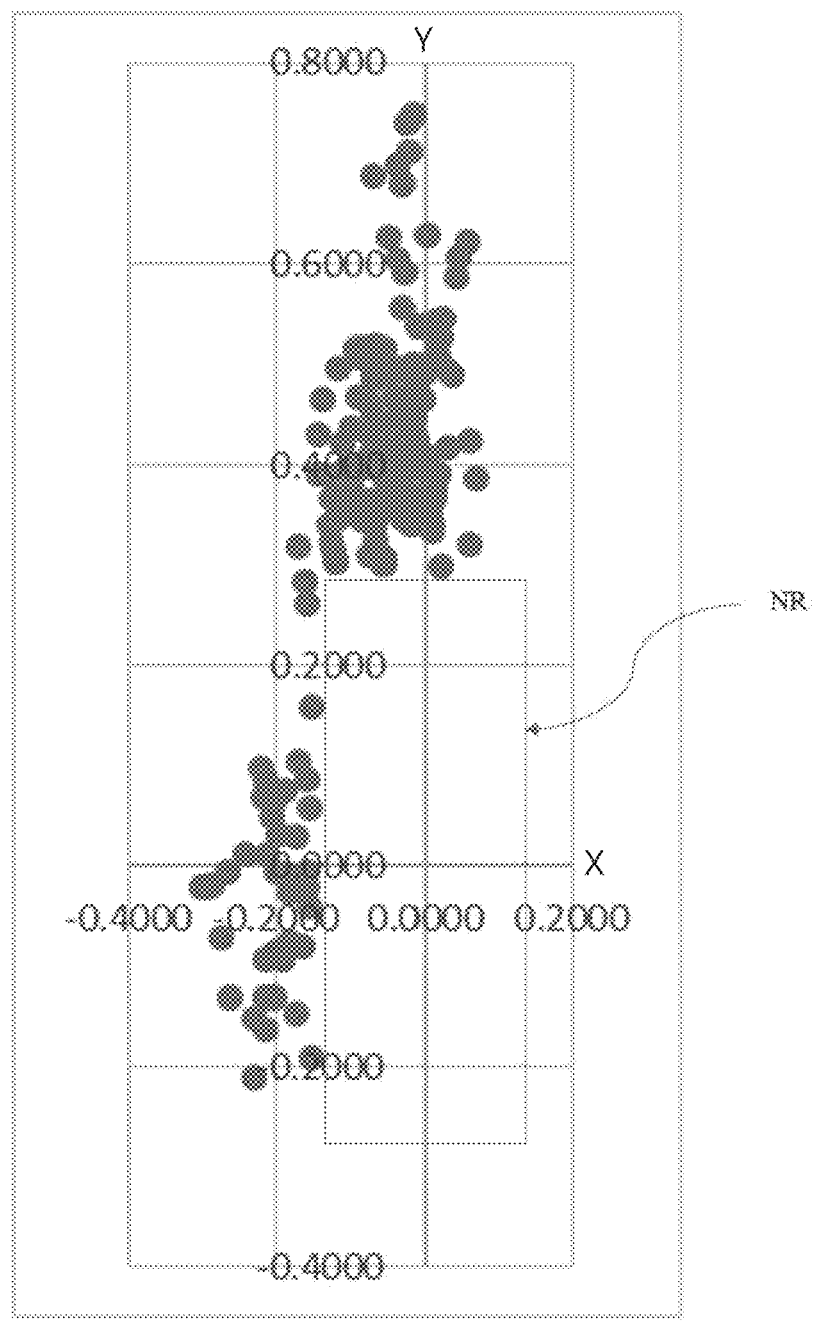
FIG. 24 is a distribution diagram illustrating abnormal COG values excluding normal COG values in a normal range (NR) among the COG values included in the distribution diagram of FIG. 23 according to the present disclosure.

FIG. 24 is a distribution diagram illustrating the distribution of abnormal COG values excluding the COG values in a normal range "NR" among the COG values included in the distribution diagram of FIG. 23. For example, a predetermined CGx range and a predetermined CGy range can be set as the normal range NR by analyzing the distributions of the COG values of the normal persons, and in the example illustrated in FIG. 24, a range of –0.15 inches to +0.15 inches is set as the normal CGx range, a range of –0.3 inches to +0.3 inches is set as the normal CGy range, and only the abnormal COG values excluding the COG values included in the normal range NR are illustrated. As can be seen in FIG. 24, when the normal COG values are excluded, the COG values affecting the balance of the patient are concentrated on the +X+Y plane, the –X+Y plane, and the –X–Y plane.

Figure 25:
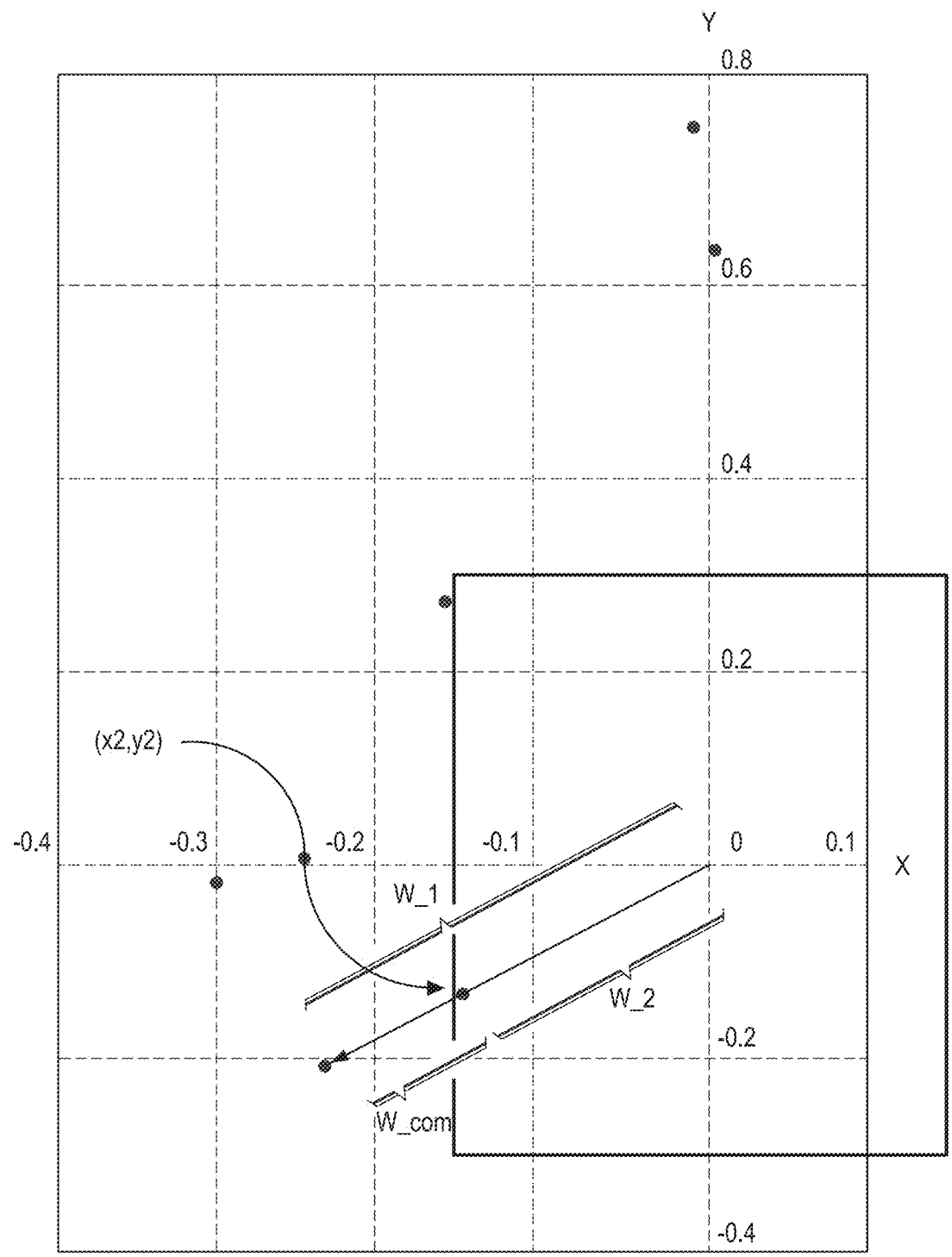
FIG. 25 is a graph illustrating representative compensation target COG values affecting the balance of a patient among the abnormal COG values included in the distribution diagram of FIG. 23 according to the present disclosure.

FIG. 25 is a graph illustrating representative compensation target COG values affecting the balance of the patient among the abnormal COG values included in the distribution diagram of FIG. 24. The compensation target COG values can be obtained by dividing the COG coordinate system by 30° to obtain 12 directions as illustrated in FIG. 6 and extracting the COG value having the largest vector value (size) (the largest square root value of a sum of CGx squared and CGy squared) or the largest W1 (the largest square root value ($\sqrt{(Wx^2+Wy^2)}$)) of a sum of Wx squared and Wy squared) in each direction.

Here, a total of 12 directions are directions in which the torso of the patient shakes or the patient loses the balance, and the number of directions is not limited to 12. The number of directions may be 8, 16, or any other even number. A direction to which each COG value belongs can be identified by calculating an angle of the COG value (CGx, CGy) using Formula (5).

$$A \text{ TAN } 2(CGx, CGy) \times 180/PI( ) \qquad (5)$$

The COG coordinate system of the patient is divided into 12 directions or 12 angle ranges: 0 to 30°, 30 to 60°, 60° to 90°, 90° to 120°, 120° to 150°, 150° to 180°, –0° to –30°, –60° to –90°, –90 to –120°, –120° to –150°, and –150° to –180°. The graph having the points or the COG values illustrated in FIG. 26 is obtained by extracting the COG value with the largest vector value or the largest W1 in each angle range. Herein, 0 to 30°, 30 to 60°, 60° to 90°, 90° to 120°, 120° to 150°, 150° to 180°, –0° to –30°, –60° to –90°, –90 to –120°, –120° to –150°, and –150° to –180° correspond to the area F, the area E, the area D, the area C, the area B, the area A, the area G, the area H, the area I, the area J, the area K, and the area L illustrated in FIGS. 6 to 8. Different angle ranges may set, for example, –15 to 15°, 15 to 45°, 45° to 75°, . . . 165° to –165°, –15° to –45°, . . . , and –135° to –165°.

FIG. 26 is a table for describing a method of determining the weight size and the weight placement position using the points of the COG values illustrated in FIG. 25. In FIG. 26, x1 and y1 indicate CGx and CGy of each of the COG values illustrated in FIG. 25, respectively, and W_1 indicates a weight corresponding to each the COG value.

x2 and y2 indicate x and y coordinates of an intersection between an imaginary line connecting the origin O and the COG value (x1, y1) and the normal range NR (e.g., the normal CGx range and the normal CGy range), and W-2 indicates a weight corresponding to (x2, y2). W_com indicates a weight for balance compensation and is obtained by subtracting W_2 from W_1 (W_1–W_2). W_com for balance compensation in each direction can be obtained by subtracting W_2 belonging to the normal range (NR) from W_1 of each of the COG values illustrated in FIG. 25.

In FIG. 26, a total weight of W_com is determined to be 3.115 pounds (lb), but it may be too heavy for a patient with a body weight of 106 lb. Therefore, 2.8 pounds (lb) is determined as a weight size from the weight size range (W1 to W2) obtained above. W_com % indicates a percentage of W_com in each direction with respect to the sum of W_com in all the directions. % input is a filed in which the operator can input a value, and for example, when the operator inputs 2.5, 2.5% of the body weight of the patient is input as an input value, and 2.8 lb is input as an input value. Thereafter, weights corresponding to W_com % in the respective directions are determined as the weight sizes. The weight size can be determined based on W_com illustrated in FIG. 26, but it can be determined by taking the weight size range (W1 to W2) obtained above into consideration on the basis of a ratio in each direction (indicated in percentage (W_com %) in FIG. 26). In addition, it may be determined in consideration of the weight size range (W1 to W2) obtained above based on a ratio of W_1 in each direction (indicated in percentage (W_1%) in FIG. 26).

Further, the operator may determine the total weight size within 3% of the body weight of the patient and determine the weight size and the weight placement position based on the ratio (W_com %) of W_com or the ratio (W_1%) of W_1 illustrated in FIG. 27.

In FIG. 26, y1/x1 indicates a slope of each COG value, and a function of y2=a/b×x2 is used to calculate x2 and y2, and y1/x1 is used to determine whether an imaginary line segment connecting each COG value (CGx, CGy) with the origin intersects the normal CGx range or the normal CGx range. If the absolute value of b/a (or y1/x1) is greater than 2 since ±0.15 inches and ±0.3 inches are used as the normal CGx range and the normal CGy range, the imaginary line segment is determined to intersect the normal CGy range, and otherwise it is determined to intersect the normal CGx range. Accordingly, ±0.3 is used as y2 depending on the sign of y1 when the absolute value of b/a (or y1/x1) is greater than 2, ±0.15 is used as x2 depending on the sign of x1 when the absolute value of b/a (or y1/x1) is less than 2, and ±0.15 and ±0.3 are used as x2 and y2 depending on the sign of x1 and the sign of y1 when the absolute value of b/a (or y1/x1) is equal to 2.

FIG. 27 is a diagram illustrating an example in which weight sizes and the weight placement positions determined as described above are indicated in the balance compensating vest illustrated in FIGS. 7 and 8. As illustrated in FIG. 27, the weight size and the weight placement position determined as described above may be displayed in 2D or 3D of a torso shape of human on a display screen. Accordingly, since the weight size and the weight placement position determined are displayed as illustrated in FIG. 27, the operator can easily make the balance compensating vest while viewing only such a display screen, whereby the balance dysfunction of the patient can be corrected accurately.

When the patient wearing the balance compensating vest with the weight size and the weight placement position presented as illustrated in FIG. 27 stands on the platform 10C of the body center measuring apparatus 100, the process illustrated in FIGS. 23 to 26 is repeated, and, thus, it can be understood whether or not the body center values fall within the normal range (NR), and the tremor of the patient can be measured through the COGy value fluctuation graph 1200 and the COGx value fluctuation graph 1300.

In a case in which the tremor occurs in the patient in the placement of FIG. 27, if the abnormal peak values illustrated in the COGy value fluctuation graph 1200 and the COGx value fluctuation graph 1300 are anterior peak values, the weights of 0.81 pounds and 1.1 pounds are distributed to the position corresponding to T7 to T9 of the thoracic vertebrae, e.g., the sub-area J2 and the sub-area I2 or the sub-area J1 and the sub-area I1 so that the tremor falls within the normal range.

Further, when the patient has the rotational balance dysfunction, fine adjustment is performed by distributing the weights of 0.81 pounds and 1.1 pounds to the sub-area J2 and the sub-area I2 or the sub-area J1 and the sub-area I1. This is because, as described above, when the weight is placed in J1 and I1, the force pulling the torso of the patient is stronger than when the weight is placed in J3 and I3.

Further, when the patient wearing the balance compensating vest with the weight size and the weight placements presented as illustrated in FIG. 27 stands on the platform 10C of the body center measuring apparatus 100, the body center distribution diagram similar to that illustrated in FIG. 23 is obtained, the total weight size determined as illustrated in FIG. 26 based on W_com % may be reduced when all the coordinates indicating the body center are within the normal range NR, whereas the total weight size determined as illustrated in FIG. 26 based on W_com % may be increased when all the coordinates indicating the body center are outside the normal range NR.

Although the balance compensation procedure of determining the weight size and the weight placement position described with reference to FIGS. 23 to 27 has been described as being performed using the body center measuring apparatus 100, the present disclosure is not limited to this example. Any other sensor apparatus can be used instead of the body center measuring apparatus 100 as long as a distribution diagram similar to that illustrated in FIG. 23 can be generated using measurement values (for example, x and y coordinate values) of the sensor apparatus, the measurement values (x and y coordinate values) affecting the balance of the patient can be extracted in a predetermined number of directions through a filtering process similar to that illustrated in FIGS. 24 and 25, and the percentage (%) of the weight size (W_com) in each direction can be obtained.

For example, a 9-axis sensor having a 3-axis accelerometer function, a 3-axis gyroscope function, and a 3-axis magnetometer function to which a predetermined filter (for example, a Kalman filter) is applied can be used.

More specifically, a distribution diagram similar to that illustrated in FIG. 23 is generated using measurement values (for example, x and y coordinate values) of the 9-axis sensor, measurement values (x and y coordinate values) affecting the balance of the patient are extracted in a predetermined number of directions through a filtering process similar to that illustrated in FIGS. 24 and 25, the percentage (%) of the weight size (W_com) of each of the measurement values affecting the balance of the patient in a predetermined number of directions is obtained, and the weight size (W_com) in each direction is obtained by applying a weight of a predetermined percentage of the body weight of the patent (for example, within 3% of the body weight of the patient) to the percentage (%) of the weight size (W_com) of each of the measurement values affecting the balance of the patient.

In some embodiments, the process of generating the distribution similar to that illustrated in FIG. 23 may be omitted, and measurement values (x and y coordinate values) affecting the balance of the patient among the measurement values (for example, x and y coordinate values) of the 9-axis sensor may be extracted in a predetermined number of directions through a filtering process similar to that illustrated in FIGS. 24 and 25, the percentage (%) of the weight size (W_com) of each of the measurement values affecting the balance of the patient in a predetermined number of directions may be obtained, and the weight size (W_com) in each direction may be obtained by applying a weight of a predetermined percentage of the body weight of the patent (for example, within 3% of the body weight of the patient) to the percentage (%) of the weight size (W_com) of each of the measurement values affecting the balance of the patient.

The 9-axis sensor may have a wireless connectivity function, for example, a Bluetooth function. In this case, the measurement can be performed while the patient is standing or walking. The normal range RM can be obtained by analyzing the distributions of the measurement values (x and y coordinate values) of the normal persons. The measurement values (x and y coordinates) affecting the standing/walking balance of the patient can be extracted by applying the filtering process using the normal range RM.

Accordingly, the balance compensation performance can be remarkably improved as the weight size and the weight placement positions can be determined in a predetermined number of directions using the measurement values obtained while the patient is walking.

Figure 29:
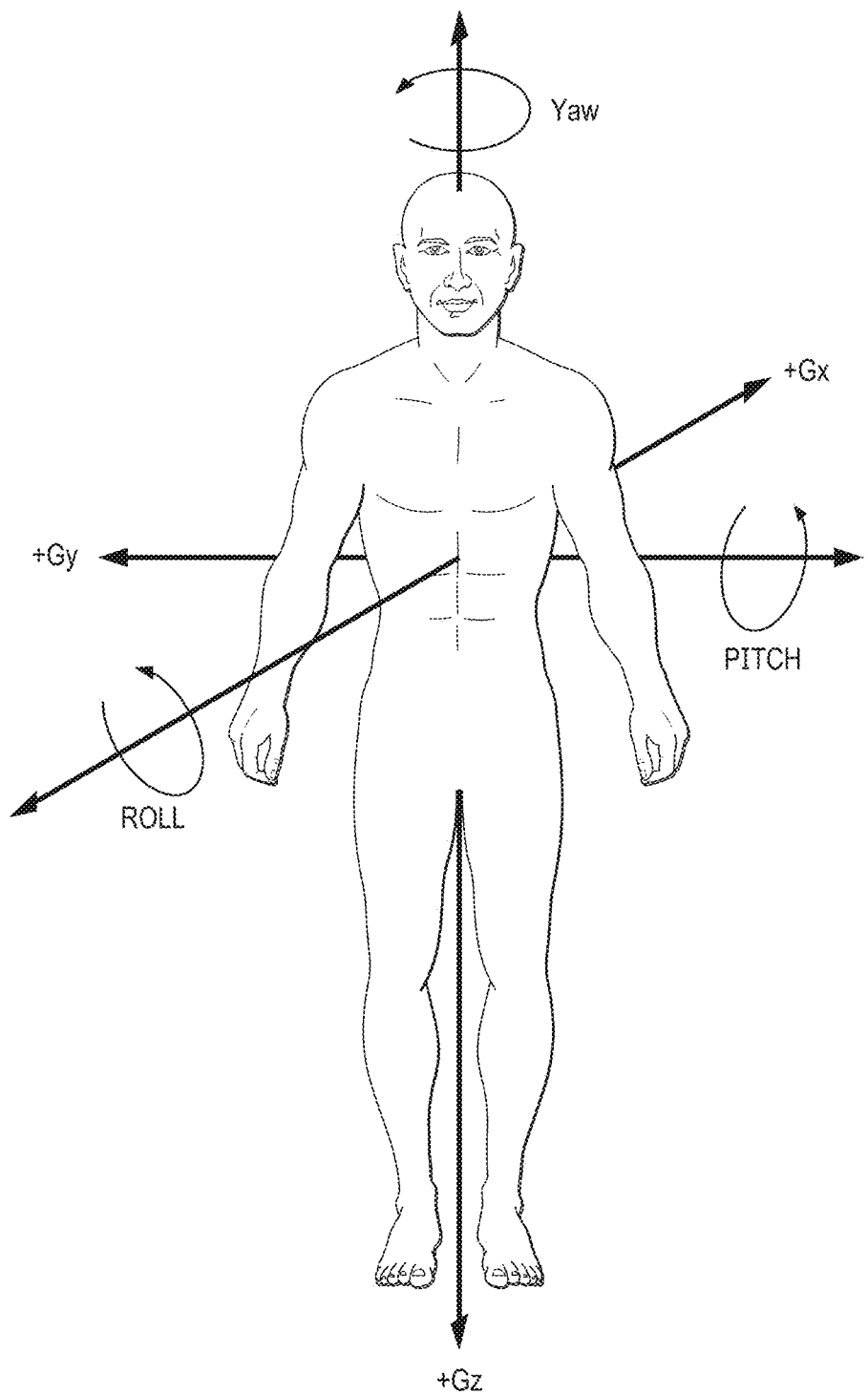
FIG. 29 is a diagram illustrating yaw, pitch, and roll angles of humans calculated using a 9-axis sensor.

More specifically, FIG. 29 is a diagram illustrating yaw, pitch, and roll angles of humans calculated using the 9-axis sensor. Using the 9-axis sensor, the body center can be obtained by obtaining yaw, pitch, and roll angles in a state in which the 9-axis sensor is attached to the torso of the patient.

A normal range NR for balance (tremor) compensation in the technique using the 9-axis sensor can be set by obtaining yaw, pitch, and roll angles of normal persons while the normal persons are standing or walking for a predetermined time in a state in which the 9-axis sensor is attached to the torso of the patient. The yaw, pitch, and roll angles of the 9-axis sensor can be obtained by applying a predetermined filter process (for example, a Kalman filter, a quaternion complementary (Q-COMP) filter, a quaternion gradient descent (Q-GRAD) filter, or the like) using the accelerometer function, the gyroscope function, and the magnetometer (compass) function.

In order to provide the balance compensating device to the patient having the balance dysfunction, the yaw, pitch, and roll angles of the patient are measured while the patient is standing or walking for a predetermined time while the 9-axis sensor is attached to the torso of the patient.

A three-dimensional distribution diagram similar to that illustrated in FIG. 23 is generated using the yaw, pitch, and roll angles of the patient measured for a predetermined time. Abnormal yaw, pitch, and roll angles affecting the balance of the patient are extracted through a filtering process using the normal range NR, similarly to FIG. 24.

As illustrated in FIG. 29, the yaw angle, in relation to a human body, indicates a rotation angle around the spine of the human body as the axis. As such, the yaw angle also indicates the measurement value of a balance dysfunction patient, and such measurement value (e.g., yaw angle) will correspond to any one of the 12 areas illustrated in FIG. 6. Alternatively, an angle indicating any one of the 12 areas illustrated in FIG. 6 may be obtained using Formula (6) using the roll angle and the pitch angle as x and y values, respectively. The pitch angle indicates an angle in which the torso of the person is shaking in the anteroposterior direction, and the roll angle indicates an angle in which the torso of the person is shaking in the lateral direction.

The representative abnormal yaw, pitch, and roll angles affecting the balance of the patient are extracted, for example, by extracting yaw, pitch, and roll angels having the largest vector length in each of a predetermined number of directions, similarly to FIG. 25.

The percentage (%) of the weight size (W_com) of each of the measurement values (the yaw, pitch, and roll angles) affecting the balance of the patient is obtained using the vector lengths.

The weight size (W_com) in each direction may be obtained by applying a weight of a predetermined percentage of the body weight of the patent (for example, within 3% of the body weight of the patient) to the percentage (%) of the weight size (W_com) of each of the measurement values affecting the balance of the patient.

Further, when the above-described measurement is performed while the patient wearing the balance compensating vest with the weight size and the weight placements presented as illustrated in FIG. 27 is standing or walking, the pitch angles and the roll angles can be obtained, and the total weight size determined as illustrated in FIG. 26 based on W_com % may be reduced when all the coordinates indicating the pitch angles and the roll angles are within the normal range NR, whereas the total weight size determined as illustrated in FIG. 26 based on W_com % may be increased when all the coordinates indicating the pitch angles and the roll angles are outside the normal range NR.

The x and y coordinate values may be obtained as the measurement values using the accelerometer function in a state in which the patient is standing, and a process similar to that illustrated in FIGS. 23 to 27 may be applied.

As described above, the type of sensor device used for balance compensation is not limited to the sensors described in the present disclosure as long as it is possible to extract measurement values affecting the balance of the patient in at least one direction, obtaining the percentage (%) of the weight size (W_com) in each direction, and determining the weight size to be placed on the basis of the percentage (%) of the weight size (W_com) in each direction. For example, the sensor device may be a 3D body scanning device.

Although the balance (tremor) compensating vest to which the weight is attachable using hook and loop fasteners has been described as the balance (tremor) compensating device in the above as an example, the present disclosure is not limited thereto. The weight may be attached to the patient's body using any other suitable materials. In the case of the vest with the hook and loop fastener, there may be many issues and problems in using the hook and loop fastener as attaching/detaching material. For example, there may be a ventilation issue and the fastener may restrict the freedom of movement of the vest when the patient wears the vest. In addition, the weight may be separated from the vest, for example, when the fastener is worn out.

Figure 30:
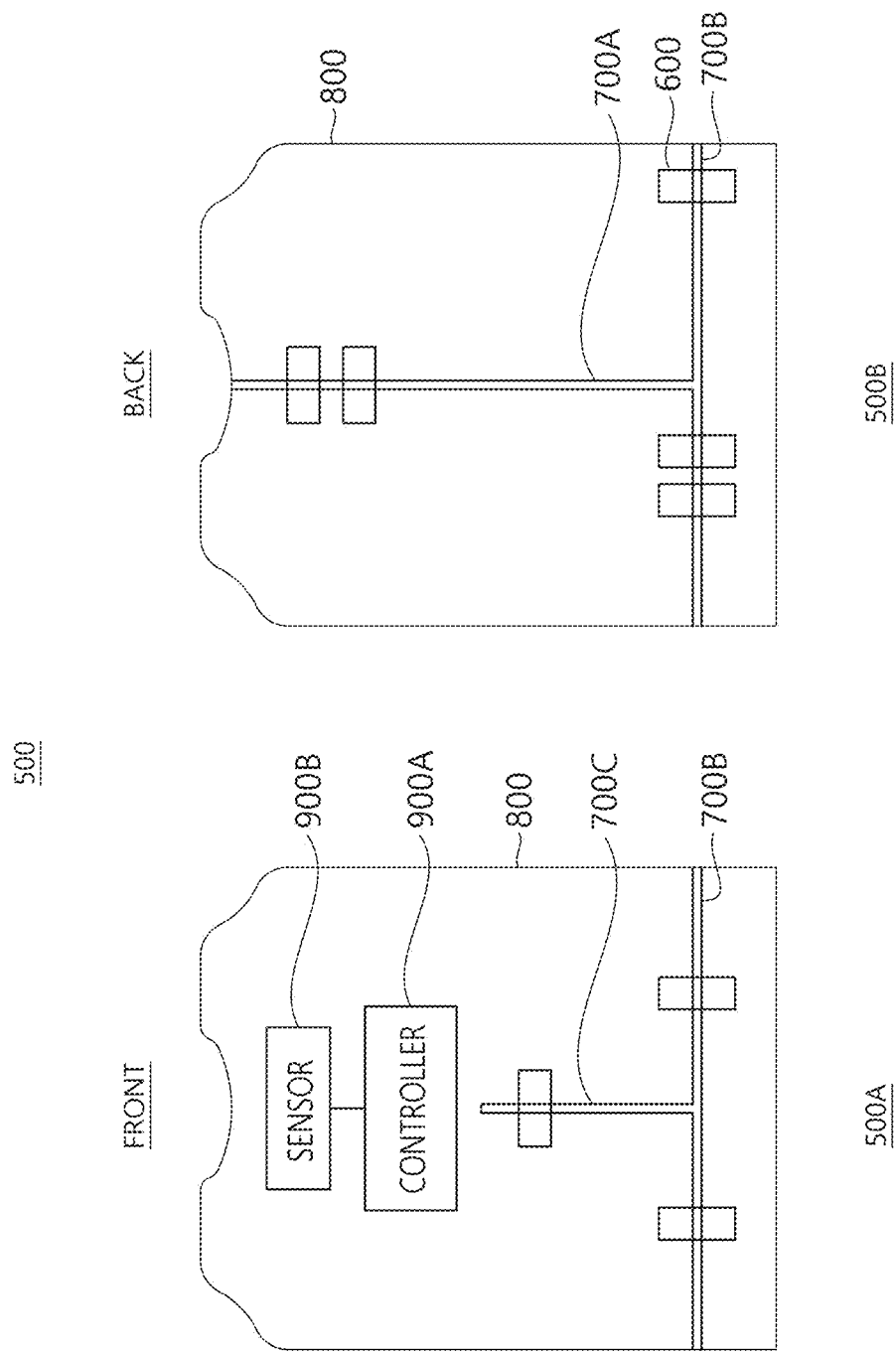
FIG. 30 is a diagram illustrating another example of a balance (tremor) compensating device according to the present disclosure.

FIG. 30 is a diagram illustrating another example of a balance (tremor) compensating device. The balance compensating device has a vest form as illustrated in FIG. 30 but may have any form for supporting the torso, and a form of the balance compensating device is not limited.

A balance compensating device 500 includes a front side 500A and a back side 500B. Each of the front side 500A and the back side 500B includes a structure 800, at least one rail 700 fixed to the inside of the structure 800, and at least one weight 600 movably fixed to the rail 700.

The structure 800 is worn on the torso of the patient and supports the torso of the patient and may be made of fabric as in a vest or may be made of plastic as in a brace or an orthotic.

The rail 700 serves to provide a path along which the weight 600 is able to move slidably. To this end, the weight 600 includes a part which connects with the rail 700 and moves slidably, and the weight 600 is fit into the rail 700 and able to move in a vertical direction along vertical rails 700A and 700C or move in a horizontal direction along a horizontal rail 700B. At least one rail is formed as the vertical rails 700A and 700C, and at least one rail is formed as the horizontal rail 700B.

The weight 600 may have an affixing mechanism capable of affixing the weight 600 to the rail 700 such as a screw. The weight 600 may be affixed to the rail 700 with the affixing mechanism by the user, and in this case, the vertical or horizontal movement of the weight 600 is restricted.

The balance compensating device 500 may further include a control unit 900A, a sensor unit 900B such as the 9-axis sensor described above, an actuator 600A installed in the weight 600, and a storage unit that stores a program for realizing the functions of the information processing device 200 described above to provide the balance compensation program. The control unit 900A implements the balance dysfunction function, the weight size determining function, the weight placement position determining function, the body center calculating function, and the body center value fluctuation calculating function by executing the program.

The actuator 600A installed in the weight 600 moves the weight 600 along the rail 700 in response to a control signal transmitted from the control unit 900A in a wired or wireless manner. The control signal may be wirelessly transmitted from the control unit 900A to the actuator 600A using, for example, Bluetooth (a registered trademark). The control signal may be transmitted from the control unit 900A to the actuator 600A using the rail 700 as a wired transmission line.

The sensor unit 900B measures the measurement value (for example, the yaw, pitch, and roll angles) of the patient while the patient is standing or walking and transmits the measurement value (for example, the yaw, pitch, and roll angles) of the patient to the control unit 900A in real time.

The control unit 900A determines whether or not the measurement value (for example, the yaw, pitch, and roll angles) of the patient is within the normal range NR. When the measurement value (for example, the yaw, pitch, and roll angles) of the patient is within the normal range NR, the control unit 900A continuously monitors whether or not the measurement value (for example, the yaw, pitch, and roll angles) of the patient is within the normal range NR.

However, when the measurement value (for example, the yaw, pitch, and roll angles) of the patient is out of the normal range NR, the control unit 900A determines a direction (or an angle range) and the weight size corresponding to the measurement value (for example, the yaw, pitch, and roll angles) of the patient, and controls the actuators 600A such that the weights 600 corresponding to the determined weight size is moved to a position corresponding to the determined direction (or the determined angle range), so that the balance dysfunction of the patient is improved. The balance compensation operation can be continuously performed while the patient is standing or moving, and, therefore, the patient's balance dysfunction can be dynamically compensated.

Further, the control unit 900A may measure the tremor (the COG value fluctuation or the fluctuation of the yaw, pitch, and roll angles) of the patient while the patient is standing or walking and control the actuator 600A such that the tremor of the patient is reduced when the tremor (the COG value fluctuation or the fluctuation of the yaw, pitch, and roll angles) of the patient is out of the normal range NR.

In the configuration in which the weight 600 is moved by the actuator 600A, preferably, a pair of rails 700 are installed so that the weight 600 can be moved bi-directionally.

In addition, a rail housing of a cylindrical shape or a rectangular tunnel shape may be installed to cover the rail 700 so that the movement of the weight 600 is not disturbed.

In the configuration in which the weight 600 is moved by the actuator 600A in response to a control signal from the control unit 900A, when the patient wears the balance compensating device 500 for the first time, the control unit 900A automatically determines the percentage of the weight size in each direction and the weight placement positions using the above-described method and causes the weights 600 to be moved through the actuator 600A in accordance with the percentage of the weight size in each direction and the weight placement position which are determined. Accordingly, different weight sizes and different weight placement positions can be determined in accordance with a daily heath state or a biorhythm of the patient since the health state of the patient may change daily.

Thereafter, the control unit 900A continuously monitors whether or not the measurement value (for example, the yaw, pitch, and roll angles) of the patient is within the normal range NR and performs the balance compensation procedure as described above.

The total weight size initially included in the balance compensating device 500 is preferably, 3% or less than the body weight of the patient.

Figure 31:
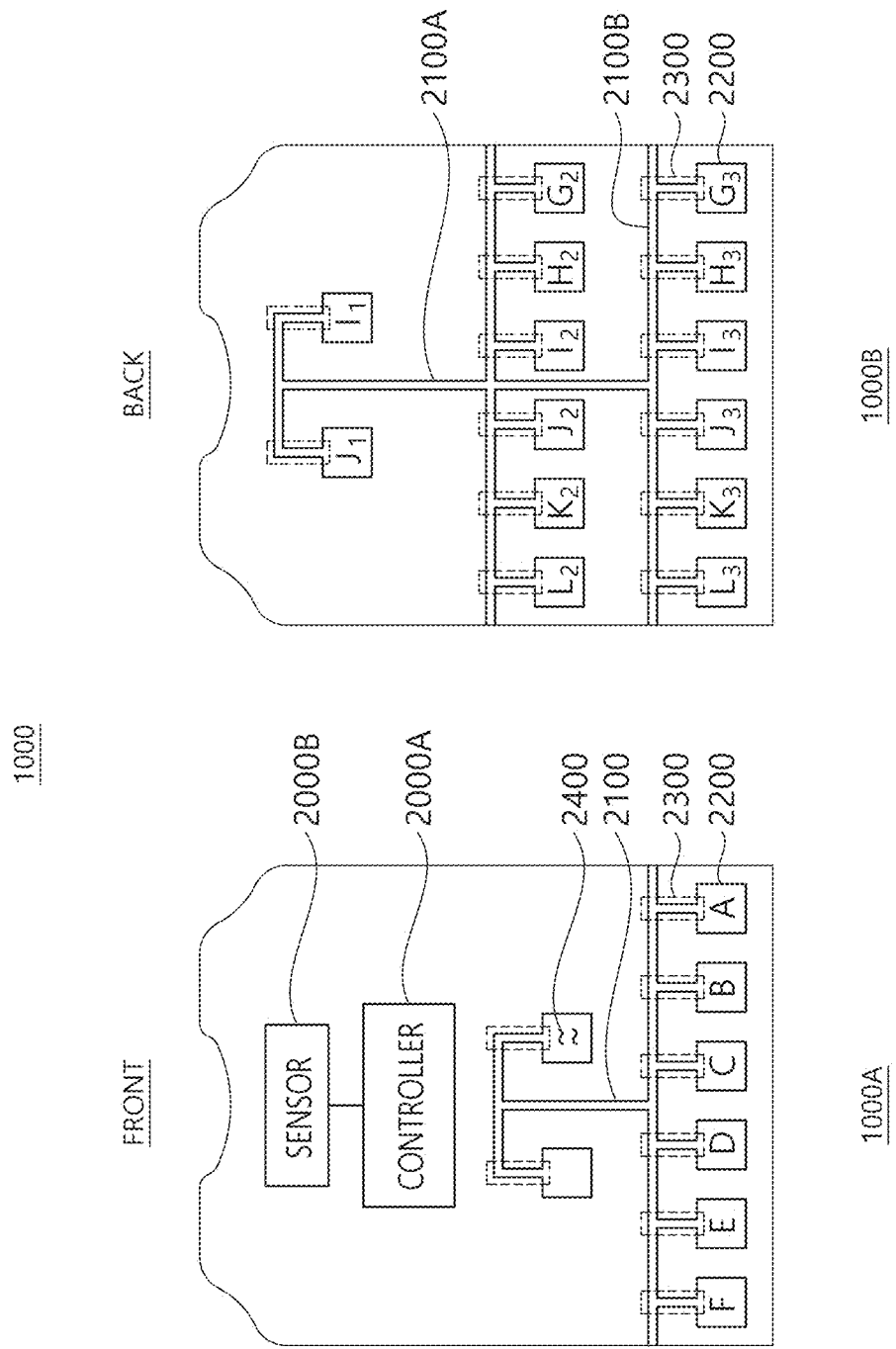
FIG. 31 is a diagram illustrating another example of a balance compensating device according to the present disclosure.

As another example, liquid may be used as the weight 600. FIG. 31 is a diagram illustrating another example of a balance compensating device according to the present disclosure.

A balance compensating device 1000 includes a front side 1000A and a back side 1000B. Each of the front side 500A and the back side 500B includes a structure 800, at least one liquid channel 2100 fixed to the inside of the structure 800, at least one liquid pocket 2200 connected with the liquid channel 2100, at least one pump 2300, and liquid 2400.

The structure 800 is worn on the torso of the patient and supports the torso of the patient and may be made of fabric as in a vest or may be made of plastic as in a brace or an orthotic.

The liquid channel 2100 serves to provide a channel along which the liquid 2400 is able to move. The liquid channel 2100 includes at least one vertical channel 2100A and at least one horizontal channel 2100B. Preferably, a pair of channels are installed so that the liquid 2400 can be moved bi-directionally as each of the vertical channel 2100A and the horizontal channel 2100B. The horizontal channel 2100B on the front side may be connected with the horizontal channel 2100B on the back side.

The pump 2300 serves to move the liquid 2400 between the liquid pockets 2400 in response to a control signal from a control unit 900A.

The liquid pocket 2200 stores the liquid 2400, and the liquid pockets 2400 which correspond in number to the areas or the sub-areas illustrated in FIG. 6 are preferably formed. The positions of the liquid pockets 2400 preferably correspond to the areas or the sub-areas illustrated in FIG. 6.

The balance compensating device 1000 includes a control unit 2000A, a sensor unit 2000B such as the 9-axis sensor described above, and a storage unit that stores a program for realizing the functions of the information processing device 200 described above to provide the balance compensation program. The control unit 2000A implements the balance dysfunction function, the weight size determining function, the weight placement position determining function, the body center calculating function, and the body center value fluctuation calculating function by executing the program.

The pump 2300 is preferably installed corresponding to each liquid pocket 2200 and injects or ejects the liquid 2400 which is the weight in response to a control signal transmitted from the control unit 2000A in a wired or wireless manner into or from the liquid pocket 2200.

The control signal may be wirelessly transmitted from the control unit 2000A to the pump 2300 using, for example, Bluetooth. The control signal may be transmitted from the control unit 2000A to the pump 2300 using the liquid channel 2100 as a wired transmission line.

The sensor unit 2000B measures the measurement value (for example, the yaw, pitch, and roll angles) of the patient while the patient is standing or walking and transmits the measurement value (for example, the yaw, pitch, and roll angles) of the patient to the control unit 2000A in real time.

The control unit 2000A determines whether or not the measurement value (for example, the yaw, pitch, and roll angles) of the patient is within the normal range NR. When the measurement value (for example, the yaw, pitch, and roll angles) of the patient is within the normal range NR, the control unit 2000A continuously monitors whether or not the measurement value (for example, the yaw, pitch, and roll angles) of the patient is within the normal range NR.

When the measurement value (for example, the yaw, pitch, and roll angles) of the patient is out of the normal range NR, the control unit 2000A determines a direction (or an angle range) and the weight size corresponding to the measurement value (for example, the yaw, pitch, and roll angles) of the patient, and controls the pumps 2300 such that the liquid 2400 corresponding to the determined weight size is moved to a position corresponding to the determined direction (or the determined angle range), so that the balance dysfunction of the patient is improved. The balance compensation operation can be continuously performed while the patient is standing or moving, and, therefore, the patient's balance dysfunction can be dynamically compensated.

Further, the control unit 2000A may measure the tremor (the COG value fluctuation or the fluctuation of the yaw, pitch, and roll angles) of the patient while the patient is standing or walking and control the pump 2300 such that the tremor of the patient is reduced when the tremor (the COG value fluctuation or the fluctuation of the yaw, pitch, and roll angles) of the patient is out of the normal range NR.

In the configuration in which the liquid 2400 is injected into or ejected from the liquid pocket 2200 and moved by the pump 2300 in response to a control signal from the control unit 2000A, when the patient wears the balance compensating device 1000, the control unit 2000A automatically determines the percentage of the weight size in each direction and the weight placement positions using the above-described method and causes the liquid 2400 to be moved between the liquid pockets 220 through the pump 2300 in accordance with the percentage of the weight size in each direction and the weight placement position which are determined. Accordingly, different weight sizes and different weight placement positions can be determined in accordance with a daily heath state or a biorhythm of the patient since the health state of the patient may change daily.

Thereafter, the control unit 2000A continuously monitors whether or not the measurement value (for example, the yaw, pitch, and roll angles) of the patient is within the normal range NR and performs the balance compensation procedure as described above.

The total weight size initially included in the balance compensating device 500 is preferably, 3% or less than the body weight of the patient.

According to the balance/tremor compensating device with the above configuration, the weight size and the weight placement position are not fixed, and the weight size and the weight placement position are determined in real time based on all the measurement values affecting the balance/tremor of the patient. Therefore, the balance dysfunction/tremor of the patient is corrected dynamically.

The above-described configuration of the balance/tremor compensating device is particularly useful for the providing balance compensation and/or tremor reduction for the balance dysfunction patients whose balance dysfunction marked by the changes in their COG in two or more directions without uniform pattern.

The above-described configuration of the balance/tremor compensating device is an example of how weight placements can occur dynamically in real time. In another embodiment of the present disclosure, it is possible to provide balance/tremor compensating device capable of dynamically adjusting weight size and weight placements by having liquid of certain weight move through a tube to certain locations of the balance/tremor compensating device.

Figure 28:
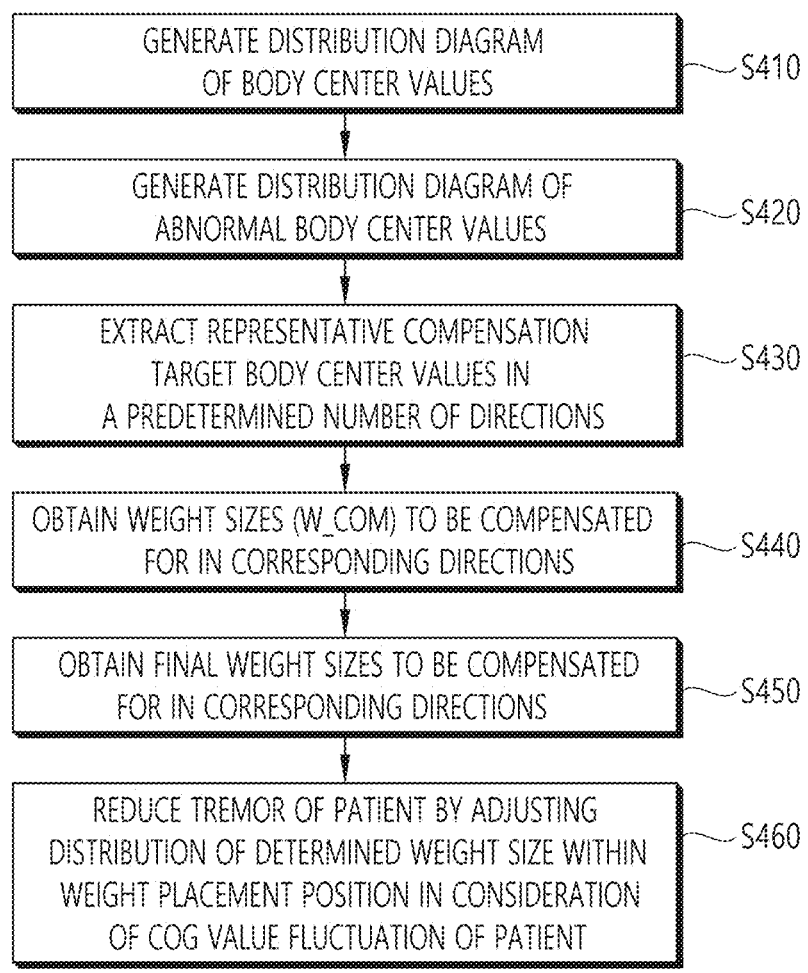
FIG. 28 is a flowchart illustrating a process of making a balance compensating vest by determining weight sizes and weight placement positions through a process illustrated in FIGS. 24 to 28 according to the present disclosure.

FIG. 28 is a flowchart illustrating the process of determining the weight size and the weight placement position and making the balance compensating vest through the process illustrated in FIGS. 23 to 27.

In step 410, the body center values (e.g., the COG values (CGx, CGy)) are obtained at intervals of a period, for example, when the patient stands on the platform 10C of the body center measuring apparatus 100 or while the patient is standing or walking with the 9-axis sensor attached to the torso, and for example, the distribution diagram of the body center values is generated.

In step 420, the distribution of the abnormal COG values excluding the COG values included in the normal range NR in the distribution diagram of the body center values is generated.

The process of generating the distribution diagrams in steps 410 and 420 may be omitted.

In step 430, the representative compensation target COG values affecting the balance of the patient among the abnormal COG values in a number of directions are extracted.

In step 440, the weight (W_com) for the balance compensation in each direction is obtained by subtracting the weight value belonging to the normal range NR from the weight value of each of the representative compensation target COG values.

In step 450, the weight size used for the balance compensation in each direction is determined in consideration of the range of the first weight size W1 and the second weight size W2. When the total weight W_com used for the balance compensation determined in step 440 is within the range of the first weight size W1 and the second weight size W2, step 450 may be omitted.

In step 460, the tremor of the patient is measured, and the tremor of the patient is reduced by adjusting the distribution of the weight size within each area in consideration of the COG value fluctuation of the patient without changing the basic weight placement position, e.g., by moving the position of the weight up or down within the determined area.

As described above, according to the present disclosure, it is possible to identify the balance dysfunction of the patient and determine the weight size and the weight placement position capable of compensating for the balance dysfunction, and thus, the persons without the trained knowledge in physical therapy or medicine can make the customized balance compensating vest capable of compensating for the balance dysfunction of the patient. In addition, compared to the methods currently used by physical therapists or medical professionals, the time needed to test and make a balance compensation vest is reduced.

In addition, the present disclosure allows the operator and the patient to confirm the correction and reduction of balance dysfunction and tremor while the patient is wearing the balance vest, and therefore, the present disclosure also allows the patient and the operator to make adjustments to the weight placement and weight size selection without many trials.

The present disclosure has been described above using the balance compensating vest as an example of the balance compensating device, but it is merely an example, and the present disclosure can be applied to any device which can be attached to a patient's body or worn by a patient, and such device may be in the form of garment, orthotic, or brace as long as the balance dysfunction of the patient can be compensated in accordance with the weight size and the weight placement position determined by the technique disclosed in the present disclosure.

While the descriptions in the present disclosure focus on the balance compensation, separate and independent apparatus or system can be implemented for measuring and improving tremors based on the present disclosure.

While various embodiments in accordance with the disclosed principles have been described above, it should be understood that they have been presented by way of example only, and are not limiting.

Furthermore, the above advantages and features are provided in described embodiments, but shall not limit the application of such issued claims to processes and structures accomplishing any or all of the above advantages.

Although the invention(s) is/are described herein with reference to specific embodiments, various modifications and changes can be made without departing from the scope of the disclosure. Accordingly, the specification and figures are to be regarded in an illustrative rather than a restrictive sense, and all such modifications are intended to be included within the scope of the present disclosure. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms "a" and "an" are defined as one or more unless stated otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

The invention claimed is:

1. A system comprising:
    at least one sensor configured to determine measurements of at least one of a weight, pressure, or rotation angle of at least a portion of a person, or combinations thereof, over a period of time and for a plurality of directions; and
    at least one non-transitory storage medium having instructions stored thereon for causing the system to:
    determine a plurality of data points indicating lateral movement and anteroposterior movement of the at least the portion of the person based on the measurements of the at least one sensor;
    classify the plurality of data points into the plurality of directions;
    determine a representative data point representing at least one of balance, tremor, or combinations thereof of the at least the portion of the person from the classified data points for each of the plurality of directions to consequently determine representative data points; and
    determine a placement location and a size of each of a plurality of weights on a wearable article to compensate for the at least one of balance, tremor, or combinations thereof based on the representative data points to consequently determine a determined placement location of each of the plurality of weights;
    wherein: (a) the wearable article is configured to be worn by the person and includes a plurality of locations that correspond to the determined placement location of each of the plurality of weights; (b) the plurality of data points includes at least three data points that exist simultaneously; (c) the representative data points include at least two representative data points that are unequal to each other; and (d) the plurality of data points includes a first number of data points and the representative data points include a second number of data points, the second number of data points being less than the first number of data points.

2. The system of claim 1, wherein the at least one non-transitory storage medium has instructions stored thereon for causing the system to:
    determine a direction of one of the representative data points;
    determine the placement location of a first of the plurality of weights based on the direction of the one of the representative data points.

3. The system of claim 2, wherein the at least one non-transitory storage medium has instructions stored thereon for causing the system to:
    determine a magnitude of the one of the representative data points;
    determine the size of the first of the plurality of weights based on the magnitude of the one of the representative data points.

4. The system of claim 3, wherein the one of the representative data points is included in the plurality of data points indicating lateral movement and anteroposterior movement.

5. The system of claim 3, wherein the at least one non-transitory storage medium has instructions stored thereon for causing the system to:
    determine a normal range of the plurality of data points indicating lateral movement and anteroposterior movement of the at least the portion of the person to determine a determined normal range;
    determine the one of the representative data points based on the determined normal range.

6. The system of claim 5, wherein the normal range includes: (a) a lateral normal range to determine whether the one of the representative data points is normal or abnormal for the lateral movement, and (b) an anteroposterior normal range to determine whether the one of the representative data points is normal or abnormal for the anteroposterior movement.

7. The system of claim 6, wherein the lateral normal range is different from the anteroposterior normal range.

8. The system of claim 7, wherein the one of the representative data points is outside at least one of the lateral normal range, the anteroposterior normal range, or combinations thereof.

9. The system of claim 3, wherein the at least one sensor includes at least of a weight sensor, a gyro sensor, a force plate, a load cell, or combination thereof.

10. A system comprising:
at least one sensor configured to determine measurements of at least one of a weight, a pressure, or a rotation angle of at least a portion of a person, or combinations thereof over a period of time and for a plurality of directions; and
at least one non-transitory storage medium having instructions stored thereon for causing the system to:
determine a plurality of data points indicating lateral movement and anteroposterior movement of the at least the portion of the person based on the measurements of the at least one sensor;
classify the plurality of data points into the plurality of directions;
determine a normal range of the plurality of data points indicating lateral movement and anteroposterior movement of the at least the portion of the person to determine a determined normal range;
determine a representative data point representing at least one of balance, tremor, or combinations thereof of the at least the portion of the person from the classified data points for each of the plurality of directions to consequently determine representative data points; and
determine one of the representative data points based on the determined normal range;
determine a direction and a magnitude of the one of the representative data points;
determine a placement location and a size of each of a plurality of weights on a wearable article to compensate for the at least one of balance, tremor, or combinations thereof based on the representative data points to consequently determine a determined placement location of each of the plurality of weights;
determine the placement location of a first of the plurality of weights based on the direction of the one of the representative data points,
determine the size of the first of the plurality of weights based on the magnitude of the one of the representative data points;
wherein the wearable article is configured to be worn by the person and includes a plurality of locations that correspond to the determined placement location of each of the plurality of weights.

11. The system of claim 10, wherein the one of the representative data points is included in the plurality of data points indicating lateral movement and anteroposterior movement.

12. The system of claim 10, wherein the normal range includes: (a) a lateral normal range to determine whether the one of the representative data points is normal or abnormal for the lateral movement, and (b) an anteroposterior normal range to determine whether the one of the representative data points is normal or abnormal for the anteroposterior movement.

13. The system of claim 12, wherein the lateral normal range is different from the anteroposterior normal range.

14. The system of claim 13, wherein the one of the representative data points is outside at least one of the lateral normal range, the anteroposterior normal range, or combinations thereof.

15. The system of claim 10, wherein the at least one sensor includes at least of a weight sensor, a gyro sensor, a force plate, a load cell, or combination thereof.

16. The system of claim 10, wherein:
the plurality of data points includes at least three data points that exist simultaneously;
the representative data points include at least two representative data points that are unequal to each other;
the plurality of data points includes a first number of data points and the representative data points include a second number of data points, the second number of data points being less than the first number of data points.

* * * * *